(12) United States Patent
Stanley

(10) Patent No.: US 9,465,001 B2
(45) Date of Patent: Oct. 11, 2016

(54) CONDUCTIVE LIQUID PROPERTY MEASUREMENT USING VARIABLE PHASE MIXING

(71) Applicant: Bourns, Inc., Riverside, CA (US)

(72) Inventor: James Gregory Stanley, Novi, MI (US)

(73) Assignee: BOURNS, INC., Riverside, CA (US)

(*) Notice: Subject to any disclaimer, the term of this patent is extended or adjusted under 35 U.S.C. 154(b) by 0 days.

(21) Appl. No.: 14/855,027

(22) Filed: Sep. 15, 2015

(65) Prior Publication Data

US 2016/0077030 A1    Mar. 17, 2016

Related U.S. Application Data

(60) Provisional application No. 62/050,656, filed on Sep. 15, 2014.

(51) Int. Cl.
  *G01R 35/00*    (2006.01)
  *G01N 27/12*    (2006.01)
  *G01N 27/22*    (2006.01)

(52) U.S. Cl.
  CPC .......... *G01N 27/122* (2013.01); *G01N 27/228* (2013.01)

(58) Field of Classification Search
  CPC ............. G01N 27/122; G01N 27/227; G01N 27/228; G01N 33/18; G01R 35/005; G01R 27/28; G01R 27/32; G01R 27/60; G01R 1/28; G01R 1/072; G01R 1/067; G01R 1/073; G01R 23/20; G01R 31/022; G01R 31/021; G01R 31/1272; G01R 31/025; G01R 31/2886; G01R 29/24
  See application file for complete search history.

(56) References Cited

U.S. PATENT DOCUMENTS

| | | |
|---|---|---|
| 2,577,612 A | 12/1951 | Fay |
| 4,181,881 A | 1/1980 | Preikschat |
| 4,238,726 A | 12/1980 | Ichijo |
| 4,288,741 A | 9/1981 | Dechene et al. |

(Continued)

FOREIGN PATENT DOCUMENTS

| | | |
|---|---|---|
| CA | 1128772 A | 8/1982 |
| CN | 1719265 | 1/2006 |
| CN | 102147382 A | 8/2011 |

OTHER PUBLICATIONS

International Search Report and Written Opinion for Application No. PCT/US2015/050234 dated Dec. 23, 2015 (11 pages).

*Primary Examiner* — Son Le
*Assistant Examiner* — Thang Le
(74) *Attorney, Agent, or Firm* — Michael Best & Friedrich LLP

(57) ABSTRACT

A system and method for measuring an electrical characteristic of a fluid using a measuring circuit. In one implementation, the measuring circuit includes a sensing component, a current supply connected to the sensing component, a sensor switchably connected to the sensing component, an array of components switchably connected to the sensing component, and a monitoring circuit connected to the sensing component. A controller performs a calibration of the measuring circuit by switching parallel impedances in and out of the circuit while measuring voltages across the sensing component. The voltages are measured at at least two different phase angles that are determined by the calibration. Once voltages at different impedances and different phases are determined, the controller calculates a value of the electrical characteristic of the fluid by interpolating between lines of fixed capacitance or resistance.

20 Claims, 17 Drawing Sheets

(56) References Cited

U.S. PATENT DOCUMENTS

| | | |
|---|---|---|
| 4,675,596 A | 6/1987 | Smith |
| 4,751,476 A | 6/1988 | Meijer |
| 5,014,011 A | 5/1991 | Colvin |
| 5,225,783 A | 7/1993 | Suzuki et al. |
| 5,235,267 A | 8/1993 | Schoneberg et al. |
| 5,268,642 A | 12/1993 | Uchidomi |
| 5,313,168 A | 5/1994 | Ogawa |
| 5,414,368 A | 5/1995 | Ogawa et al. |
| 5,594,163 A | 1/1997 | Suzuki |
| 6,265,883 B1 | 7/2001 | Clark |
| 6,283,504 B1 | 9/2001 | Stanley et al. |
| 6,320,393 B1 | 11/2001 | Yasui et al. |
| 6,857,313 B2 | 2/2005 | Williamson |
| 7,098,674 B2 | 8/2006 | Stanley et al. |
| 7,180,306 B2 | 2/2007 | Stanley et al. |
| 7,617,055 B2 * | 11/2009 | Henry ............... G01F 1/74 702/100 |
| 7,659,731 B2 | 2/2010 | Lin et al. |
| 7,926,341 B2 | 4/2011 | Boudaoud et al. |
| 2006/0186897 A1* | 8/2006 | Niemann ............... G01N 11/16 324/633 |
| 2008/0264170 A1* | 10/2008 | Abbott ............... G01N 29/022 73/590 |
| 2010/0188111 A1 | 7/2010 | Fougere |
| 2010/0327884 A1 | 12/2010 | McCall et al. |
| 2012/0326733 A1* | 12/2012 | Kato ............... G01N 33/2852 324/674 |
| 2013/0291617 A1 | 11/2013 | Boudaoud et al. |

* cited by examiner

CONDUCTIVE LIQUID PROPERTY MEASUREMENT USING VARIABLE PHASE MIXING

CROSS-REFERENCE TO RELATED CASES

This application claims the benefit of U.S. Provisional Patent Application No. 62/050,656, filed on Sep. 15, 2014, the entire contents of which are incorporated herein by reference.

BACKGROUND

Embodiments of the invention relate to systems, sensors, and methods for measuring electrical properties of a fluid.

SUMMARY

Traditional capacitive sensors are limited in their ability to measure capacitance when a highly conductive path is parallel to the capacitance, as occurs when measuring a highly conductive fluid. One embodiment of the invention provides a system for determining a capacitance of a sensor in a fluid despite wide fluctuations in the fluid's conductivity. Certain embodiments do not depend upon active circuit components to be nearly ideal. Also, the signal controls (i.e., offsets, amplitudes, phases) do not require extremely high resolution or tight control across temperatures. In some cases, embodiments may be implemented at a lower cost than existing system and sensors.

The invention provides a low-cost system for determining the dielectric constant of a fluid, despite wide fluctuations in a fluid's conductivity. Traditional low-cost capacitive sensors are limited in their ability to measure capacitance of a sensor in a fluid when a highly conductive path is parallel to the capacitance as occurs when measuring a highly conductive fluid. The dielectric constant and conductivity of a fluid may be used to determine when the fluid has an expected set of properties. For example, the dielectric constant and the conductivity of the fluid can be used to determine the concentration levels of the fluid or if the fluid meets a quality standard.

One embodiment provides a system for determining the electrical properties of a material such as a fluid. In particular, the system determines a conductivity and capacitance of a sensor immersed in a fluid such as a diesel exhaust fluid. The system uses a measuring circuit, which includes a current source, a fixed resistor, a switching array, and an array of components. The current source supplies current to the fixed resistor and to the array of components via the switching array. The switching array determines which components of the array of components are placed in parallel to the fixed resistor for measurement. The system uses a monitoring circuit, which includes a phase shifter, a mixer, and a gain and offset module. The phase shifter produces waveforms of varying phase, which are supplied to the mixer. The system also includes a measurement space, which includes coordinate pairs of measured voltages across the fixed resistor for a series of measurements where a plurality of components are placed in parallel to the fixed resistor. When the capacitive measurement sensor is switched to connect to the current source, a location of a point in the measurement space identifies a capacitance of the capacitive measurement sensor with respect to the coordinate pairs.

Another embodiment provides a method of determining a capacitance of a sensor, which is in contact with a liquid. The method includes a sequence of steps to measure voltages across a fixed resistor for a series of measurements with a plurality of components placed in parallel to the fixed resistor. The measurements of the voltages are timed with a synchronous demodulation circuit such that signals at two phases produce an output where the signals change because of sensor capacitive changes independently of sensor resistive changes. The voltages across the fixed resistor when a capacitive measurement sensor is in parallel to the fixed resistor are measured for different phase signals. The capacitance of the capacitive measurement sensor is determined by interpolating between the voltage measurements.

Another embodiment provides a measurement system that is configured to determine various electrical characteristics of the fluid including, for example, dielectric constant and conductivity of the fluid. Using the capacitance of a sensor, a dielectric constant, or another measure related to the dielectric constant, of the fluid can be determined. The electrical characteristics of the fluid may be used to determine when the fluid has an expected set of physical properties. For example, the dielectric constant and the conductivity of the fluid can be used to determine the concentration level of the fluid or if the fluid meets a particular quality standard. In some cases, the measurement system provides the electrical properties of diesel exhaust fluid including a concentration and a purity of the diesel exhaust fluid.

Yet another embodiment provides a system for measuring an electrical characteristic of a fluid by separating a first orthogonal component of a signal change of a measurement signal and a second orthogonal component of the signal change of the measurement signal. The first orthogonal component is due to a change in resistance across a sensor and the second orthogonal component is due to a change in capacitance across the sensor. The system includes an array of components including the sensor. It also includes a mixer that mixes the measurement signal with a first phase signal and a second phase signal. The mixer outputs a first mixed signal related to the first phase signal and a second mixed signal relating to the second phase signal. The system also includes a controller that is configured to receive a signal indicative of the first mixed signal and the second mixed signal and to control the array of components to cause the signal change. Then the controller adjusts the first phase signal and the second phase signal such that when there is a change in the first orthogonal component, the first mixed signal is reduced and the second mixed signal is increased. The controller controls the array of components to cause additional signal changes and receives a plurality of mixed signals indicative of the additional signal changes at the first phase and the second phase. The controller determines the electrical characteristic of the fluid based on the plurality of mixed signals.

Yet another embodiment provides a method of measuring an electrical characteristic of a fluid with a measuring circuit that includes a sensing node, a sensor switchably connected to the sensing node, and an array of components switchably connected to the sensing node, and a controller. The method includes mixing a signal indicative of a voltage at the sensing node at a first configuration of the array of components with a first phase signal and a second phase signal to create a first set of reference signals. The signal is mixed, at a second configuration of the array of components, with the first phase signal and the second phase signal to create a second set of reference signals. The first phase signal and the second phase signal are adjusted until a relationship between the first set of reference signals and the second set of reference signals satisfies a condition. A plurality of configurations are set for the array of components. The signal is mixed with the adjusted first phase signal and the adjusted second phase signal at each of the plurality of configurations of the array of components to create a plurality of sets of reference signals. The signal is mixed with the adjusted first phase signal and the adjusted second phase signal with the sensor connected to the sensing node to create a set of measurement voltages. The electrical characteristic of the fluid are determined based on a relationship between the plurality of sets of reference signals and the set of measurement voltages.

Yet still another embodiment provides a system for measuring an electrical characteristic of a fluid. The system includes a sensing node, a sensor connected, via a switching array, to the sensing node, and an array of components connected, via the switching array, to the sensing node. The array of components includes a plurality of impedances. The system also includes a monitoring circuit connected to the sensing node. The monitoring circuit is configured to input a plurality of signals at a plurality of phases and to output a signal related to a measurement signal at the sensing node. The system also includes a controller connected to the switching array and the monitoring circuit. The controller is configured to receive the plurality of signals at the plurality of phases and set a first phase and a second phase of an input signal to the monitoring circuit. The controller is also configured to measure, at a first calibration impedance of the plurality of impedances, a first calibration voltage at the first phase and a second calibration voltage at the second phase. The controller also is configured to measure, at a second calibration impedance of the plurality of impedances, a third calibration voltage at the first phase and a fourth calibration voltage at the second phase. The first phase and the second phase are adjusted until a relationship between the first calibration voltage, the second calibration voltage, the third calibration voltage, and the fourth calibration voltage satisfies a condition. The controller is configured to adjust the plurality of impedances by controlling the switching array to connect at least one component of the array of components to the sensing node in a parallel-type connection and to determine a first set of reference signals based on the signal when the switching array is configured to couple a first measuring impedance of the plurality of impedances to the sensing node. The controller is also configured to determine a second set of reference signals based on the signal when the switching array is configured to couple a second measuring impedance of the plurality of impedances to the sensing node and to determine a set of sensor voltages based on the signal when the switching array is configured to couple the sensor to the sensing node. The controller is further configured to determine an electrical characteristic of the sensor based on the first set of reference signals, the second set of reference signals, and the set of sensor voltages.

Other aspects and embodiments of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

It should be noted that the phrase "series-type configuration" as used herein refers to a circuit arrangement where the described elements are arranged, in general, in a sequential fashion such that the output of one element is coupled to the input of another, but the same current may not necessarily pass through each element. For example, in a "series-type configuration," it is possible for additional circuit elements to be connected in parallel with one or more of the elements in the "series-type configuration." Furthermore, additional circuit elements can be connected at nodes in the series-type configuration such that branches in the circuit are present. Therefore, elements in a series-type configuration do not necessarily form a true "series circuit."

Additionally, the phrase "parallel-type configuration" as used herein refers to a circuit arrangement where the described elements are arranged, in general, in a manner such that one element is connected to another element, such that the circuit forms a parallel branch of the circuit arrangement. In such a configuration, the individual elements of the circuit may not necessarily have the same potential difference across them individually. For example, in a parallel-type configuration of the circuit it is possible for two circuit elements that are in parallel with one another to be connected in series with one or more additional elements of the circuit. Therefore, a circuit in a "parallel-type configuration" can include elements that do not necessarily individually form a true parallel circuit.

It should also be noted that the phrases related to measuring "capacitance," "resistance," "dielectric constant," "conductivity," or "electrical characteristics of a fluid" as used herein, do not necessarily require that the absolute values of those measures are calculated. These terms may refer to measures that are related to the absolute values of these measures. For example, a system the measures the "dielectric constant" of a fluid may not actually calculate the dielectric constant of a fluid, but rather it may make a measurement of a quantity, such as capacitance, that varies with the dielectric constant of the fluid. And, as a further example, measuring "capacitance" may refer to making a measurement that varies with the absolute capacitance.

Figure 1:
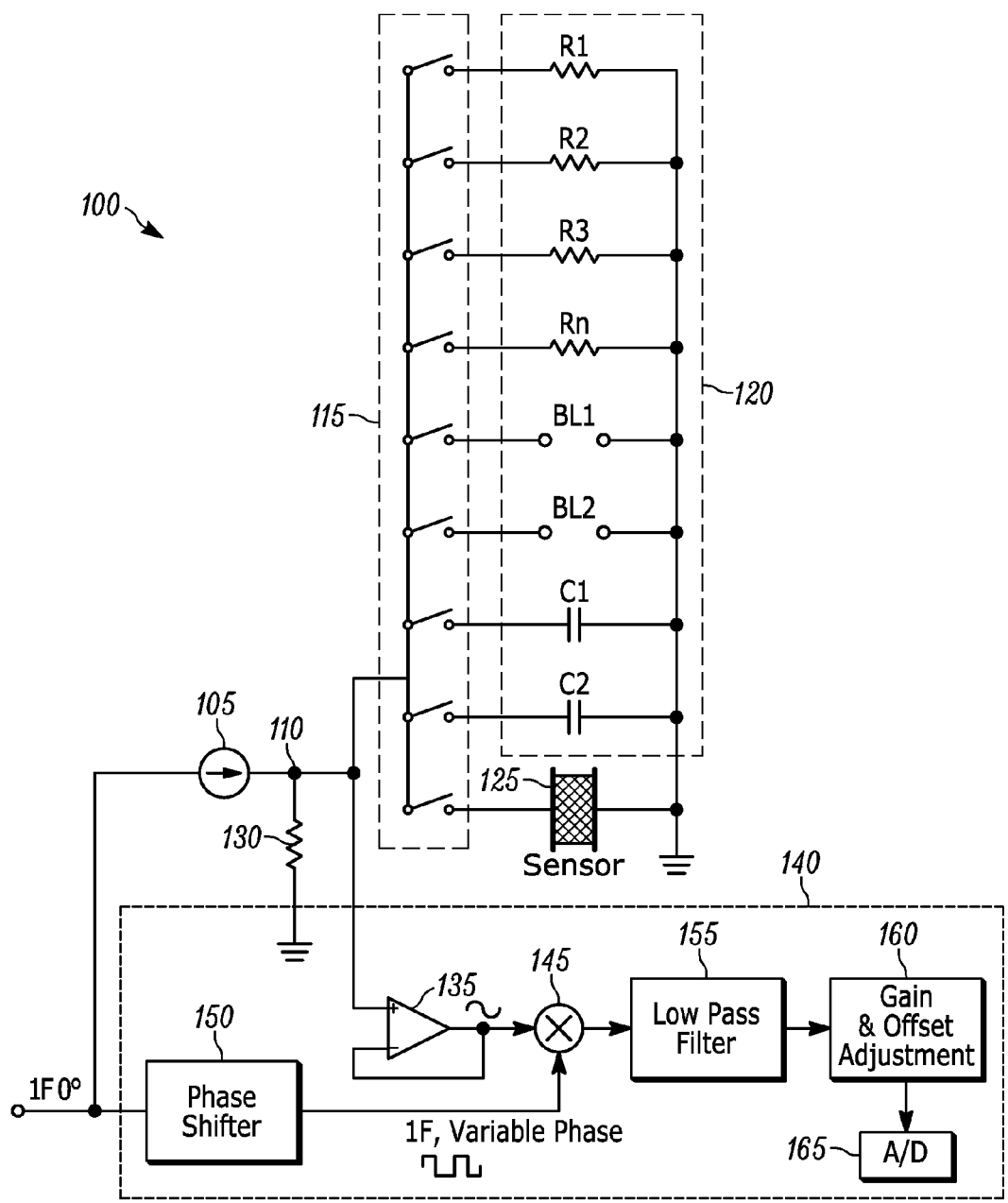
FIG. 1 is a block diagram of a measuring circuit for measuring capacitance and resistance of a fluid in accordance with one embodiment.

FIG. 1 is a block diagram of a measuring circuit 100 according to one embodiment. An output of a current source 105 (e.g., a transconductance amplifier) is connected to a sensing node 110. The sensing node 110 connects to a switching array 115. The switching array 115 connects to an array of components 120, whose other terminals are connected to ground. The array of components 120 includes a plurality of components that allow multiple impedances (Z1 ... Zn) to be selected including resistors (R1, R2, ... Rn), each having different resistances. In other embodiments, a single device can replace the plurality of resistors (R1, R2, ... Rn). In one example, a voltage-controlled, variable resistor may be used and may be implemented using a field effect transistor. The array of components 120 also includes multiple capacitors (C1 and C2). The switching array 115 also connects to one or more blank switches (BL1, BL2). The blank switches are connected to pads on a printed circuit board where no component is electrically connected. The switching array 115 also connects to a sensor 125, whose other terminal is connected to ground.

The switching array 115 creates different configurations of the array of components 120 to calibrate the measuring circuit 100 and to perform measurements. Since electronic switches contain parasitic capacitance to ground that differs depending on whether they are open or closed, they may introduce unwanted capacitance into a circuit. In the measuring circuit 100, it is desirable to have a fixed number of electronic switches while calibrating and measuring to minimize any changes of the parasitic capacitance. In that regard, the switching array 115 includes blank switches which are identical to the other switches in the switching array 115, but only connect the sensing node to empty pads on the printed circuit board. This maintains a fixed number of open and closed switches, which results in a consistent offset capacitance. The switching array 115 is controlled such that when a switch to one component (or the sensor 125) is closed, one blank switch (e.g., BL1) is open, and when two switches to two components are closed, both blank switches (e.g. BL1 and BL2) are open.

The current source 105 supplies alternating current (AC) through the sensing node 110 to a sensing component 130. In some embodiments, the sensing component 130 is a resistor having a known, or fixed, resistance value. The sensing component 130 is connected to the sensing node 110 on a first end and to ground on a second end. This configuration creates a voltage across the sensing component 130 that is dependent on the position of the switches of the switching array 115. The sensing node 110 is connected to a buffer amplifier 135 that forms the input to a monitoring circuit 140 included within the larger measuring circuit 100.

In one embodiment, the monitoring circuit 140 utilizes a synchronous demodulation circuit with gain and offset adjustment. The monitoring circuit 140 includes a buffer amplifier 135. The output of the buffer amplifier 135 is connected to an input of a mixer 145. The mixer 145 multiplies the signal from the buffer amplifier 135 with a variable-phase waveform, for example, a variable-phase square wave. The variable-phase waveform is supplied by a phase shifter 150. The output of the mixer 145 is connected to a low-pass filter 155, and the output of the low-pass filter 155 is connected to a gain and offset adjustment module 160. The output from the gain and offset adjustment module 160 is connected to an analog-to-digital converter 165 for use as a digital signal in a controller or similar electronic processor.

In some embodiments, the phase shifter 150 includes circuitry for the conversion of an oscillating waveform into another oscillating waveform (e.g., a sine wave into a square wave). In one example, the phase shifter 150 includes a sine wave to square wave comparator and a circuit to delay the square wave by a controlled interval of time. In particular, a clock or a controlled number of discrete delay stages may be used to provide the delay and, thus, the phase shift. In another example, the phase shifter 150 inputs multiple sinusoids at the same frequency and sums the sinusoids together to form an intermediate-phase sinusoid. In this example, the phase shifter 150 adjusts the amplitude of one of the input sinusoids to vary the phase of the intermediate-phase sinusoid to create a variable-phase sinusoid. This variable-phase sinusoid is then converted into a square wave for input to the mixer 145. In some embodiments, the mixer 145 is configured to perform sine wave mixing or other demodulation schemes that separate components of a signal based on their phase.

During operation of the measuring circuit 100, an oscillating current from the current source 105 is divided among several parallel-type pathways. In one example, a portion of the current may flow to the switching array 115 and through the array of components 120 depending on the state of the switching array 115. The current may also flow through the sensor 125 depending on whether the sensor 125 is connected by the switching array 115. The current also flows through the sensing component 130 to ground. When the impedance of the switched-in components of the array of components 120 is lowered, the current through the sensing component 130 is lowered, and thus the voltage across the sensing component 130 is lowered. This reduces the voltage seen by the mixer 145. When the switch to the sensor 125 is closed, a loss of current to the sensing component 130 occurs and this lowers the voltage seen by the mixer 145. In this way, a change in voltage or in the phase angle of the voltage across the sensing component 130 can be used to identify the impedance, the resistance, and/or the reactance of the sensor 125. In an ideal system, the in-phase component of the voltage (i.e., in-phase with the current) on the sensing component 130 acts as an indicator of the current due solely to resistance (i.e., resistive current) between the current source 105 and ground. The quadrature component (i.e., a 90° phase shift from the in-phase component) acts as an indicator of the current due solely to a reactive impedance (i.e., reactive current) between the current source 105 and ground. However, in practice, the impedance from the current source 105 to ground is a mix of resistive and reactive impedances. As a consequence, the phase angle between the voltage and the current will not be exactly 0° or 90°.

Figure 2A:
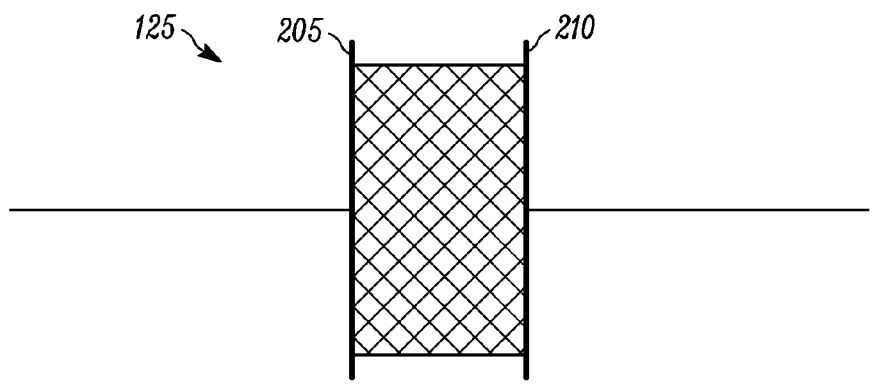
FIG. 2A is a schematic representation of a sensor in accordance with one embodiment.
Figure 2B:
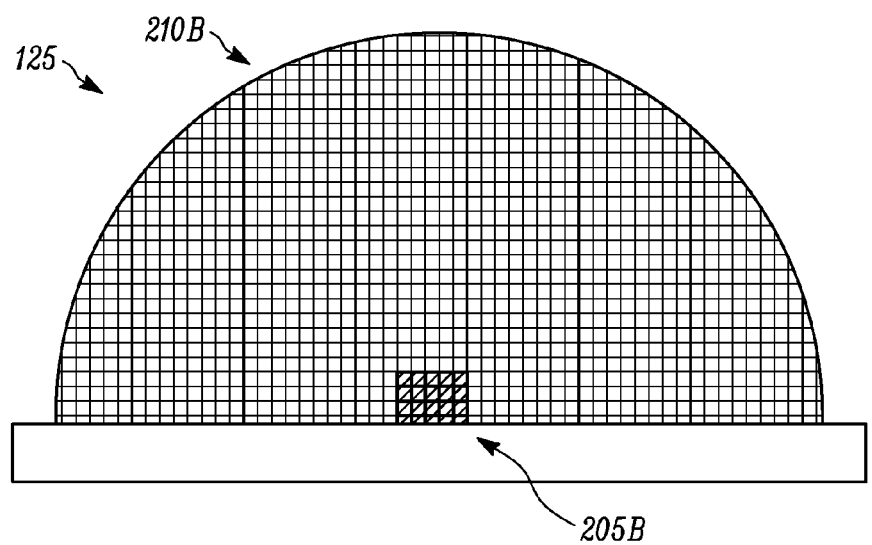
FIG. 2B is a side view of one type of the sensor.
Figure 2C:
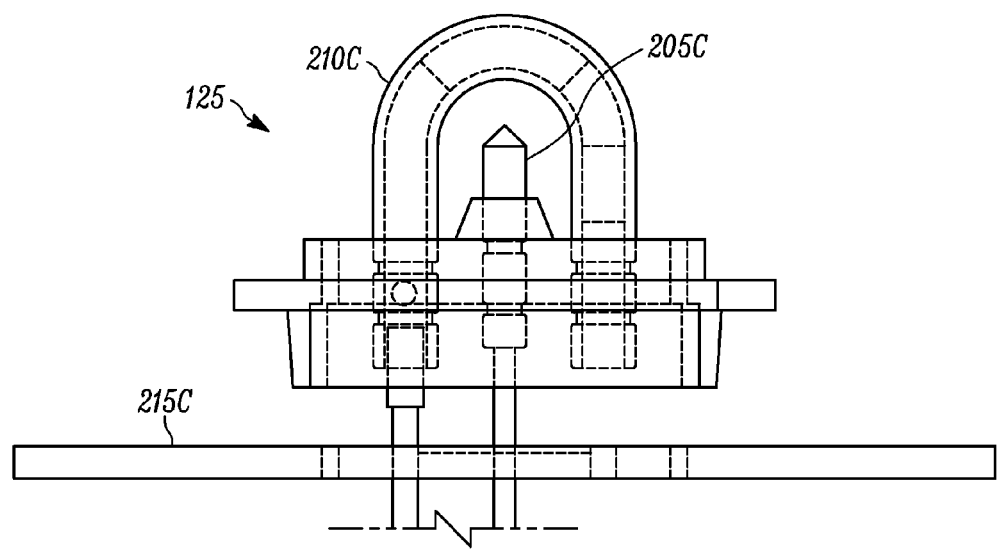
FIG. 2C is a side, partially cut-away view of one type of sensor
Figure 2D:
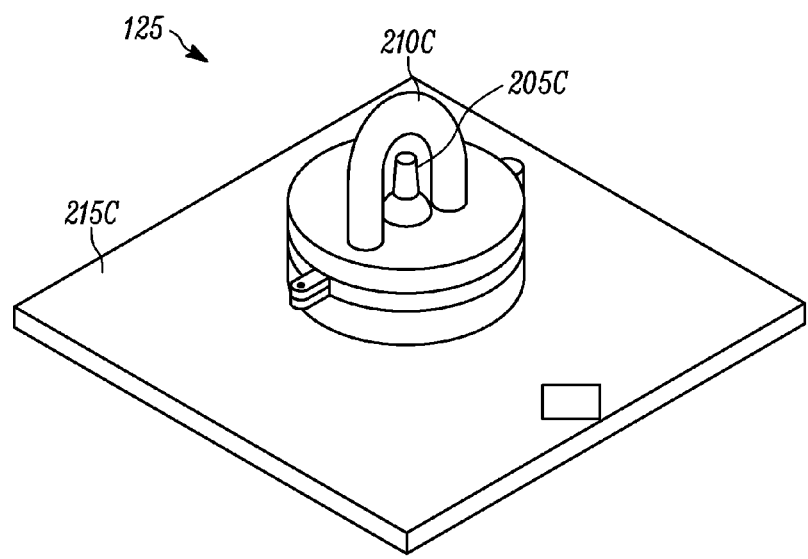
FIG. 2D is a perspective view of the sensor shown in FIG. 2C.
Figure 3A:
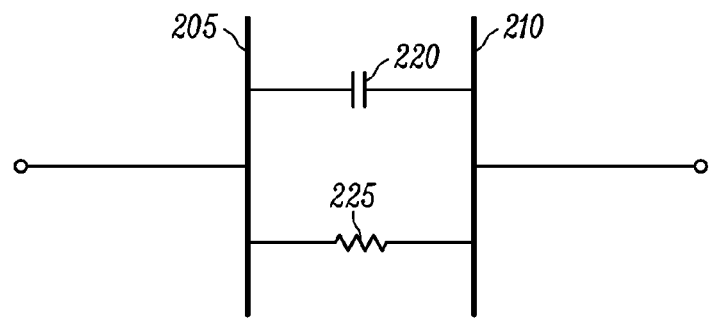
FIGS. 3A-C illustrate electrical models of sensors in accordance with certain embodiments.
Figure 3B:
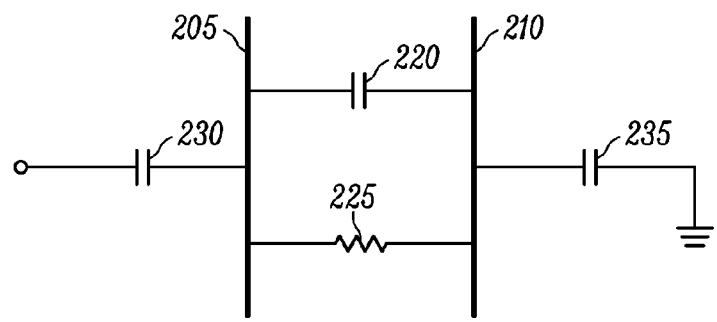

FIGS. 2A-2D illustrate a model and various aspects of the sensor 125. FIG. 2A is a schematic representation of the sensor 125. FIG. 2B schematically illustrates one implementation of the sensor 125. FIGS. 2C and 2D illustrate another implementation of the sensor 125. FIGS. 3A-3B illustrate electrical models of the sensor 125.

In the embodiments illustrated in FIG. 2A-2C, the sensor 125 includes two electrodes, a first electrode 205, 205B, 205C and a second electrode 210, 210B, 210C. In the embodiment illustrated in FIG. 2B, the first electrode 205B is covered by a spherical dome (e.g., a conductive cage). In this case, the spherical dome constitutes the second electrode 210B. In one embodiment, the second electrode 210B is formed of a screen with numerous apertures that allow fluid to pass through the second electrode 210B. In another embodiment (not shown), the second electrode 210B is formed from a contiguous sheet or solid piece of material, but is configured with a small number of apertures to allow for some fluid movement. In other embodiments, the sensor 125 may include one or more conductors that arch above a sensing electrode. For example, the embodiment of sensor 125 illustrated in FIG. 2C, includes the first electrode 205C, a second electrode 210C, and a mounting surface 215C. The mounting surface 215C may be formed of a printed circuit board (PCB). In this example, the second electrode 210C arches above the first electrode 205C. This allows fluid to flow between the first electrode 205C and the second electrode 210C. FIG. 2D is a perspective view of the sensor illustrated in FIG. 2C. It should be noted that the shape of the sensing or second electrode 210, 210B and 210C can be different from the shapes illustrated and may take other forms. The sensor 125 may be made of conductive material including, for example, stainless steel, which is generally resistant to corrosion.

Figure 3C:
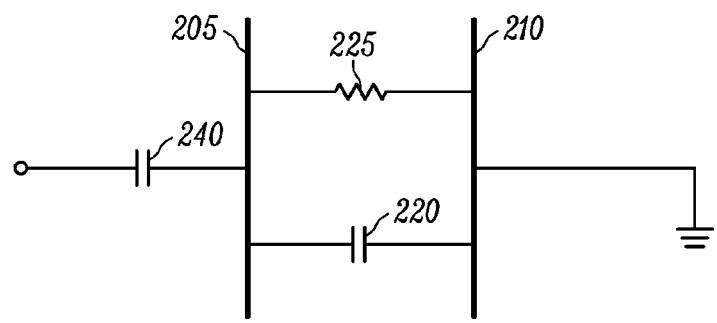

FIG. 3A illustrates an electrical model of the sensor 125 and the fluid being sensed. This model takes into account both the electrical characteristics (e.g., conductivity and dielectric constant) of the fluid between the first electrode 205 and the second electrode 210 and the geometry of the sensor 125. For example, the capacitance 220 represents the capacitance of the sensor 125 and the influence on that capacitance by the fluid in the sensor 125. Similarly, the resistance 225 represents the resistance of the sensor 125 and the influence on that resistance by the fluid in the sensor 125. Since the geometry of the sensor 125 is fixed, the capacitance 220 and the resistance 225 are values that indicate the fluid's dielectric constant and conductivity. FIG. 3B illustrates another electrical model of the sensor 125 that includes capacitance due to a surface layer being formed or deposited on the electrodes. In this model, a first electrode capacitance 230 represents the capacitance of a surface layer on the first electrode 205. The first electrode capacitance 230 reduces the total capacitance of the sensor 125. Similarly, a second electrode capacitance 235 represents the capacitance of a surface layer on the second electrode 210. The second electrode capacitance 235 reduces the total capacitance of the sensor 125. FIG. 3C represents a simplified electrical model of the sensor 125 of FIG. 3B. In the simplified model, an induced capacitance 240 represents the combination of the first electrode capacitance 230 and the second electrode capacitance 235. As the thickness of the surface layers increases, the induced capacitance 240 decreases. A decrease in the induced capacitance 240, reduces the total capacitance of the sensor 125. If the induced capacitance 240 due to the surface layers is small (corresponding to thick surface layers), the total capacitance (i.e., measured capacitance) of the sensor 125 will be strongly dependent on the thickness of the surface layer.

When the induced capacitance 240 is greater (e.g., 5 orders of magnitude greater) than the capacitance 220, accurate measurements of the capacitance 220 can be made even when the resistance 225 is relatively low. However, as the induced capacitance 240 decreases (due to thicker surface layers) relative to the capacitance 220, errors in measurement of the capacitance 220 may arise. Measurements at high frequencies (e.g., 10 MHz) may reduce the effect of this error. Conversely, measurements at low frequencies may produce errors that are dependent on the resistance, the induced capacitance 240, and the frequency. The relationship between the error and the frequency may be expressed as shown in Equation 1, below.

$$\text{Error} = MCL - ACL \propto \frac{1}{\text{frequency}^2} \quad (1)$$

where MCL is the measured capacitance of the sensor 125 and ACL is the capacitance 220. If measurements are made at two different frequencies, f1 and f2, the relationship in Equation 2 is true.

$$\frac{\text{Error}_{f1}}{\text{Error}_{f2}} = \frac{MCL_{f1} - ACL}{MCL_{f2} - ACL} \propto \frac{\frac{1}{f1^2}}{\frac{1}{f2^2}} = \frac{f2^2}{f1^2} \quad (2)$$

If measurements are made at two frequencies within a short period of time, the induced capacitance 240 and the resistance 225 may be considered constant values and the following equality in Equation 3 can be assumed.

$$\frac{MCL_{f1} - ACL}{MCL_{f2} - ACL} = \frac{f2^2}{f1^2} \quad (3)$$

The capacitance 220 may be described as shown in Equation 4.

$$ACL = \frac{\left(\frac{f2}{f1}\right)^2 * MCL_{f2} - MCL_{f1}}{\left(\frac{f2}{f1}\right)^2 - 1} \quad (4)$$

Therefore, even with a moderate surface layer on the electrodes 205 and 210, measurements at two frequencies can be used to calculate the capacitance 220. However, as the surface layer increases in thickness, the error in the measurement of capacitance across the sensor 125 becomes too large for the correction described above to work, especially when the resistance across the sensor 125 becomes small. As described in greater detail below, in one embodiment, supplemental capacitors are used to match the reference impedances to the impedance of the sensor 125 to compensate for surface layers on the electrodes (See FIG. 16).

Figure 4:
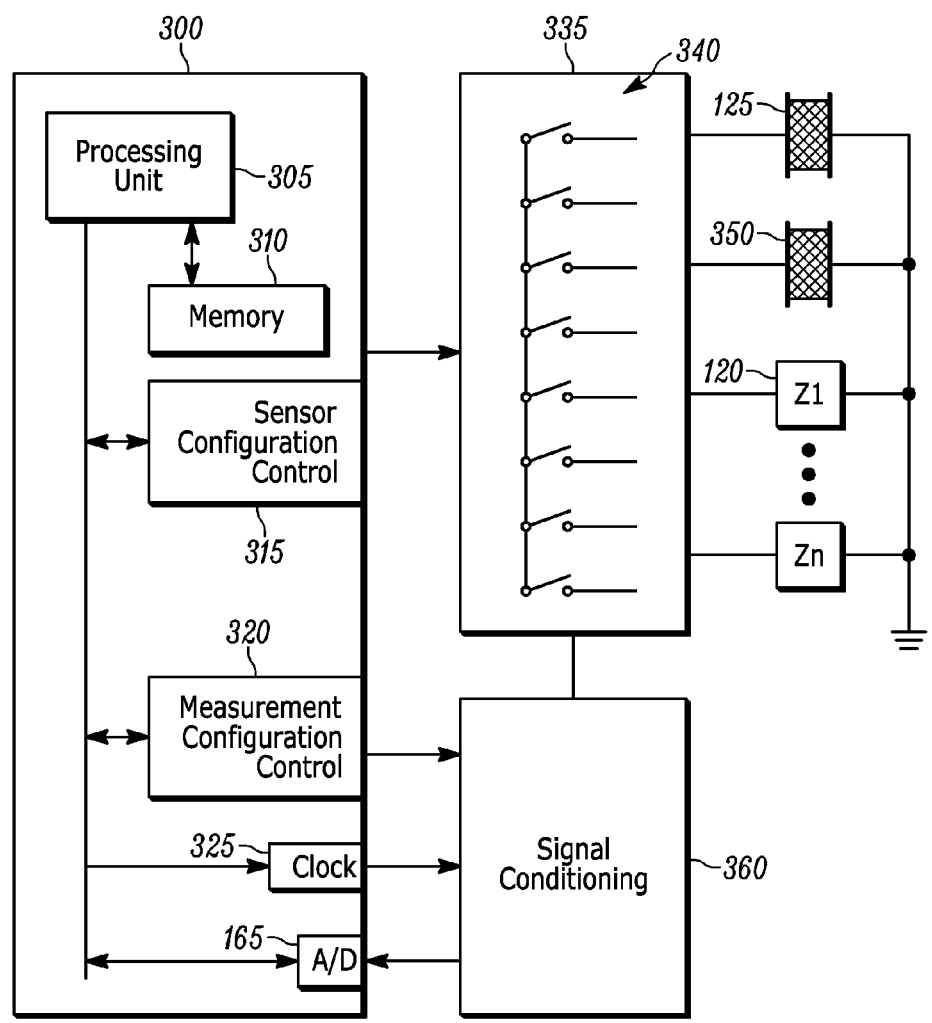
FIG. 4 is a block diagram of the measuring circuit of FIG. 1 including a controller.

FIG. 4 illustrates an exemplary controller 300 (e.g., a microcontroller, microprocessor, electronic processor, or similar device or group of devices). In the embodiment illustrated, the controller 300 includes a processing unit 305, a memory 310, a sensor configuration control 315, a measurement configuration control 320, a clock 325, and the analog-to-digital converter 165. The controller 300 is electrically connected to an alternative embodiment of the measuring circuit 100. In the example illustrated, controller 300 is connected to a sensor multiplexer 335 and a signal conditioning module 360. The sensor multiplexer 335 can be used as, or in lieu of, the switching array 115. The controller 300 includes combinations of hardware and software that are operable to, among other things, control the operation of the measuring circuit 100, control the sensor configuration control 315, and control the measurement configuration control 320. Additionally, the controller 300 is connected through the sensor multiplexer 335 to the sensor 125, an optional fluid level sensor 350, and the array of components 120 (Z1, Z2, ... Zn).

The processing unit 305, the memory 310, the sensor configuration control 315, the measurement configuration control 320, as well as the other various components are connected by one or more control or data buses or both. The use of one or more control or data buses or both for the interconnection between and communication among the various components would be known to a person skilled in the art in view of the description and drawings provided.

Figure 6:
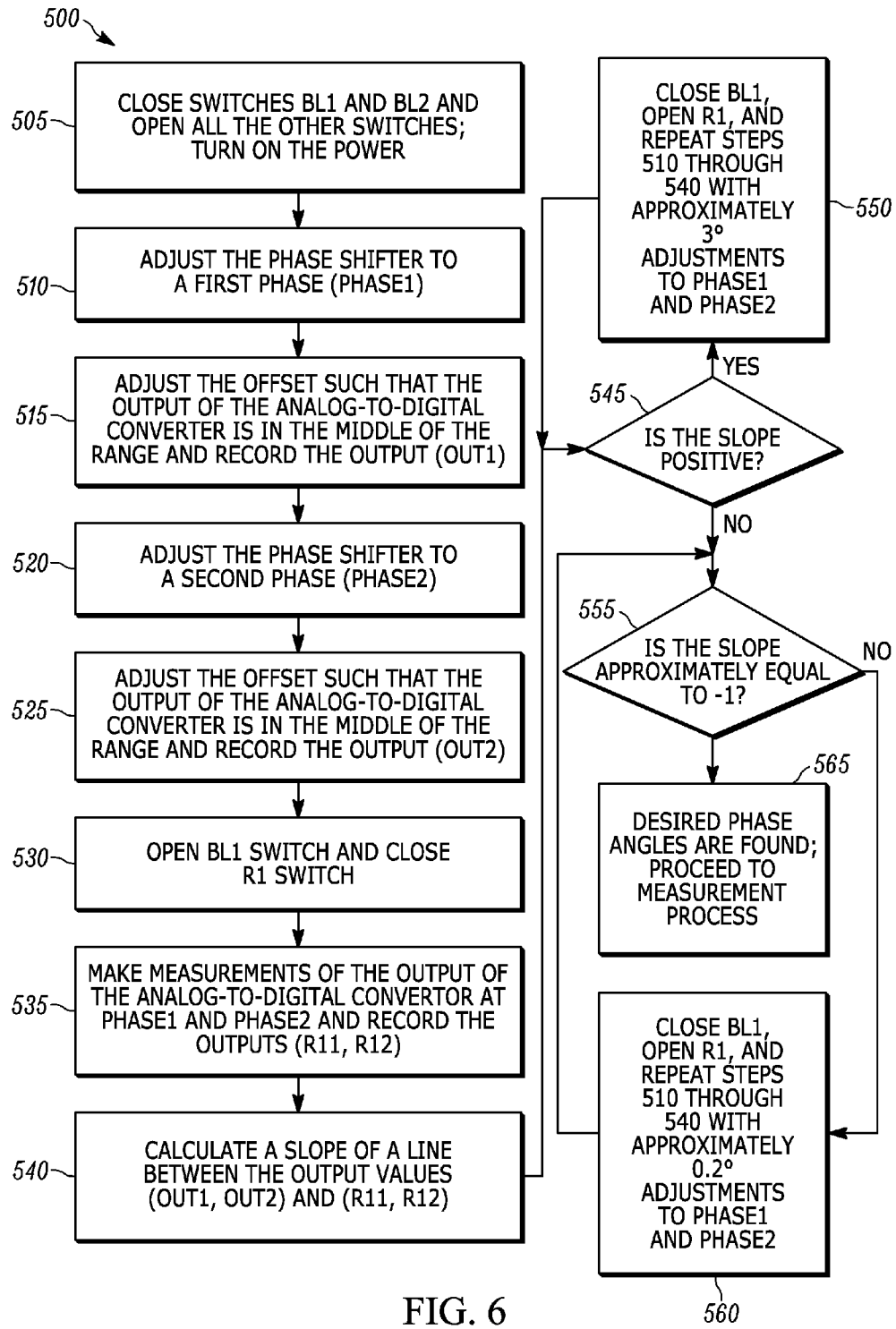
FIG. 6 is a flowchart of a method of calibrating the measuring circuit of FIG. 1.

The memory 310 includes a program storage area and a data storage area. The program storage area and the data storage area can include combinations of different types of memory 310, such as machine-readable non-transitory memory, read-only memory ("ROM"), random access memory ("RAM") (e.g., dynamic RAM ["DRAM"], synchronous DRAM ["SDRAM"], etc.), electrically erasable programmable read-only memory ("EEPROM"), flash memory, a hard disk, an SD card, or other suitable magnetic, optical, physical, or electronic memory devices. The processing unit 305 is connected to the memory 310 and executes software instructions that are capable of being stored in a RAM of the memory 310 (e.g., during execution), a ROM of the memory 310 (e.g., on a generally permanent basis), or another non-transitory computer readable medium. Software included for the processes and methods for the measuring circuit 100 can be stored in the memory 310 of the controller 300. The software can include firmware, one or more applications, program data, filters, rules, one or more program modules, and other executable instructions. For example, a method 500 (as shown in FIG. 6) effectively stores information in EEPROM about the absolute values of C1 and C2 and the geometry of the sensor 125. The processing unit 305 is configured to retrieve from memory 310 and execute, among other things, instructions related to the control processes and methods described herein. In other constructions, the controller 300 includes additional, fewer, or different components.

Figure 5:
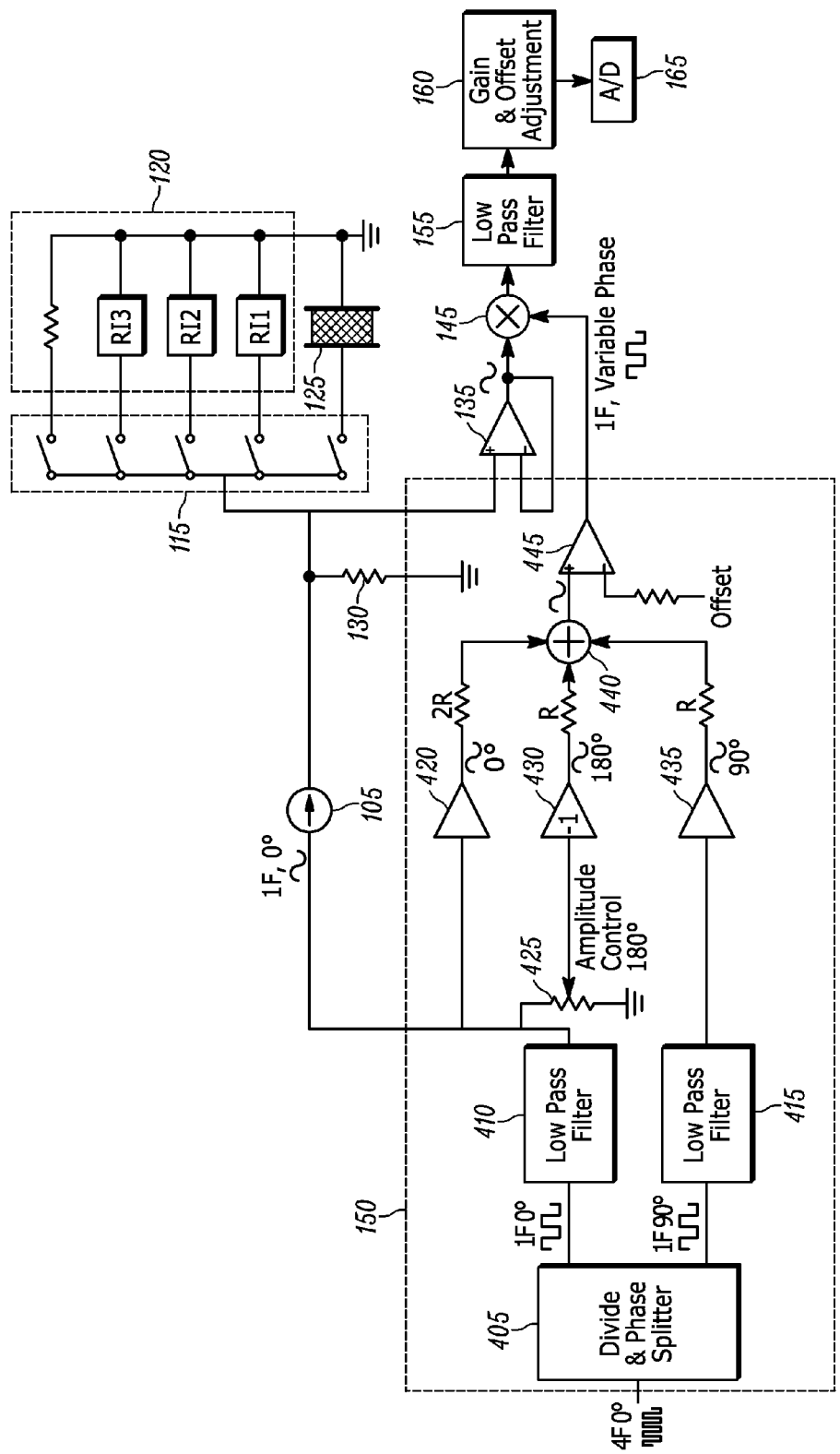
FIG. 5 is a schematic representation of a phase shifter circuit of the measuring circuit of FIG. 1 in accordance with one embodiment.

FIG. 5 illustrates the phase shifter 150 and the connections of the phase shifter 150 to the measuring circuit 100 according to one embodiment. The phase shifter 150 includes a divide and phase splitter 405 having two output connections. A first output of the divide and phase splitter 405 is connected to a first low-pass filter 410 and a second output of the divide and phase splitter 405 is connected to a second low-pass filter 415. An output of the first low-pass filter 410 is connected to an input of the current source 105, an input to a first operational amplifier 420, and an amplitude controller 425. An output of the first operational amplifier 420 is connected through a resistor (2R) to an input of a summation module 440. The output of the amplitude controller 425 is connected to an input of a second operational amplifier 430. The output of the second operational amplifier 430 is connected through a resistor (R) to an input of the summation module 440. The output of the second low-pass filter 415 is connected to a third operational amplifier 435, and the output of the third operational amplifier 435 is connected through a resistor (R) to an input of the summation module 440. The output of the summation module 440 is connected to the positive terminal of a comparator circuit 445. The output of the comparator circuit 445 is connected to the measuring circuit 100 at the input of the mixer 145.

The phase shifter 150 manipulates the response of the measuring circuit 100 by producing a plurality of phases for measurements. This can be used to create a measurement space where the signal changes caused by increases in resistive current are approximately the same amplitude and approximately orthogonal to small changes in the capacitive current. The measurement space is created by separately mixing a signal from the measurement circuit with two signals that have phases that are near to each other and are on either side of the phase angle 90° away from the angle of the current change when there is a change of resistance between the sensing node and ground. For example, if the phase angle of the current change when a resistor is connected to the sensing node is 45°, then the two phases used for a measurement might be 130° and 140° (i.e. 45°+85°=130° and 45°+95°=140°). This allows measurement of the capacitance and the resistance of the sensor 125 at the same time even when the resistive current through the sensor 125 parallel to the capacitance is unknown and may be much larger than the capacitive current through the sensor 125.

FIG. 6 is a flowchart illustrating an exemplary method 500 of determining the desired phase angles for the measuring circuit 100. Although illustrated in sequential order, steps of method 500 may be performed sequentially, simultaneously, or in a different order. The method 500 can be performed, at least in part, by the controller 300. It is possible to also perform portions of the method 500 manually. To begin, the blank switches (i.e., BL1 and BL2) are closed, all other switches of the switching array 115 are opened, and the power is turned on (step 505). The phase shifter 150 is adjusted, by the controller sending an adjustment signal, to a first phase (Phase1) (step 510). The offset of the gain and offset adjustment module 160 is adjusted such that the output of the analog-to-digital converter 165 is in the middle of the output range of the analog-to-digital converter 165 (i.e., the output of the signal conditioning module 360) and the output is recorded (OUT1) (step 515). The phase shifter 150 is adjusted to a second phase (Phase2), which may be close to Phase1 (e.g., six degrees above Phase1) (step 520). Then, the offset of the gain and offset adjustment module 160 is adjusted such that the output of the analog-to-digital converter 165 is in the middle of the output range of the analog-to-digital converter 165 and the output is recorded (OUT2) (step 525). For a given set of steps, step 505 to step 540, Phase1 and Phase2 each have their own respective offset adjustment which may remain fixed for the measurement sequence. A blank switch (e.g., BL1) is opened and the switch for R1 is closed (step 530). Outputs (R11, R12) of the analog-to-digital converter 165 for both Phase1 and Phase2 are recorded using their respective offset adjustments (step 535). A slope of a slope of a line between the outputs (OUT1, OUT2) and the outputs (R11, R12) is calculated (step 540).

Once calculated, a determination of whether the slope is positive is made (step 545). If the slope is positive, a blank switch (e.g., BL1) is closed, the switch for R1 is opened, and steps 510 through 540 are repeated (step 550). When step 510 and step 520 are triggered from step 550, the phase adjustments for Phase1 and Phase2 may be increased by a moderate amount, for example, approximately 3°. After repeating steps 510 through 540, the method returns to step 545 and determines if the slope of the line between the adjusted output values (OUT1, OUT2) and (R11, R12) is positive. If the slope is not positive, a determination of whether the slope is approximately equal to −1 is made (step 555). If the slope is not approximately equal to −1, a blank switch (e.g., BL1) is closed, the switch for R1 is opened, and steps 510 through 540 are repeated (step 560). When step 510 and step 520 are triggered from step 560, the phase adjustments for Phase1 and Phase2 may be increased by a slight amount, for example, by approximately 0.2°. After repeating steps 510 through 540, the method returns to step 555 and a determination of whether the slope of the line between the adjusted output values (OUT1, OUT2) and (R11, R12) is approximately equal to −1 is made. If the slope is approximately equal to −1, the desired phase angles (Phase1 and Phase2) have been found (step 565). As will be described in greater detail, in the example described, the phase angles determined in the method 500 are used in the measurement method 900 of FIG. 9. It should be noted that the adjustments to the phase angles triggered by step 550 and step 560 may include additional logic that aids in determining the desired phase angles by estimating an amount and direction of phase angle change for step 510 and step 520.

Figure 7:
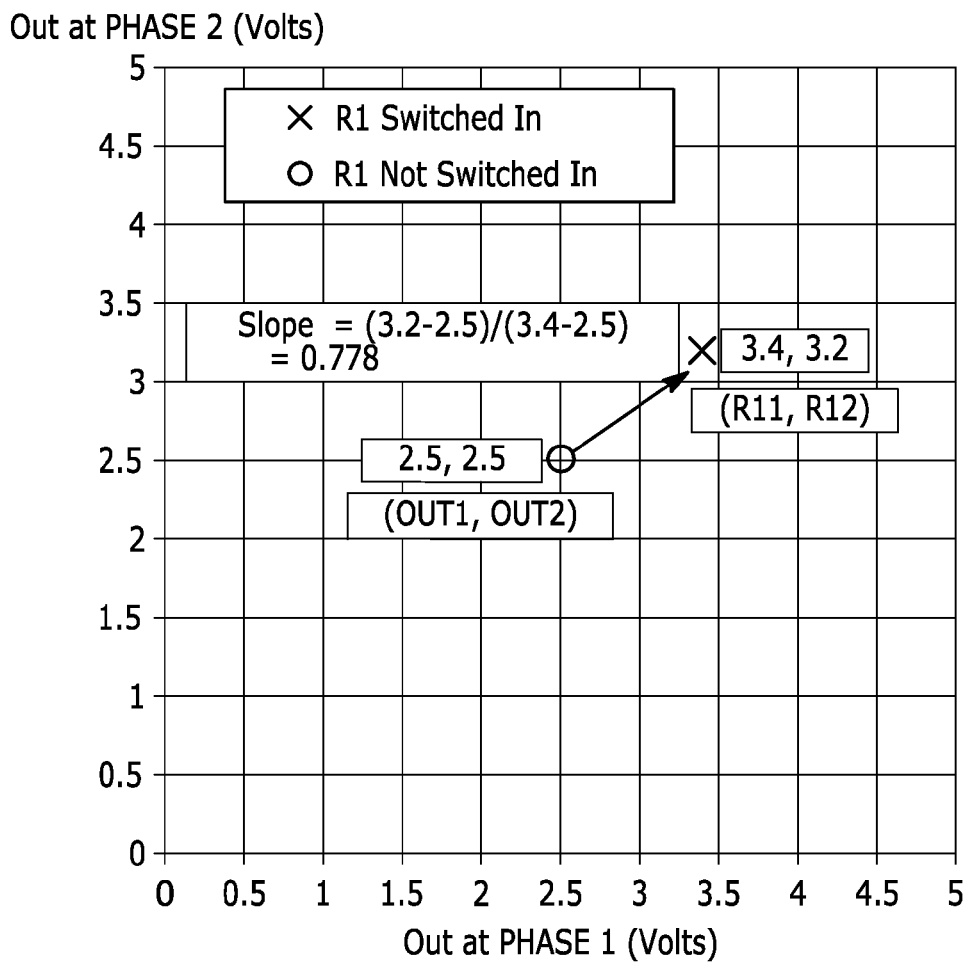
FIG. 7 is a graph illustrating reference points of output voltages of the measuring circuit of FIG. 1.

FIG. 7 is a graph illustrating an exemplary output of the signal conditioning module 360 for step 540 of the method 500. The outputs are plotted in coordinate pairs representing the measurements made at Phase1 and Phase2. The coordinate pairs represent sets of calibration signals. First, the Phase1 and Phase2 outputs (OUT1, OUT2) are plotted with only the blank switches (i.e., BL1 and BL2) closed. The Phase1 and Phase2 outputs (R11, R12) are also plotted with the switch for R1 closed and a blank switch (e.g., BL1) open. The line illustrates the slope between the coordinate pairs (OUT1, OUT2) and (R11, R12) and can be calculated by the Equation 5.

$$\text{Slope} = \frac{R12 - OUT2}{R11 - OUT1} \quad (5)$$

Figure 8:
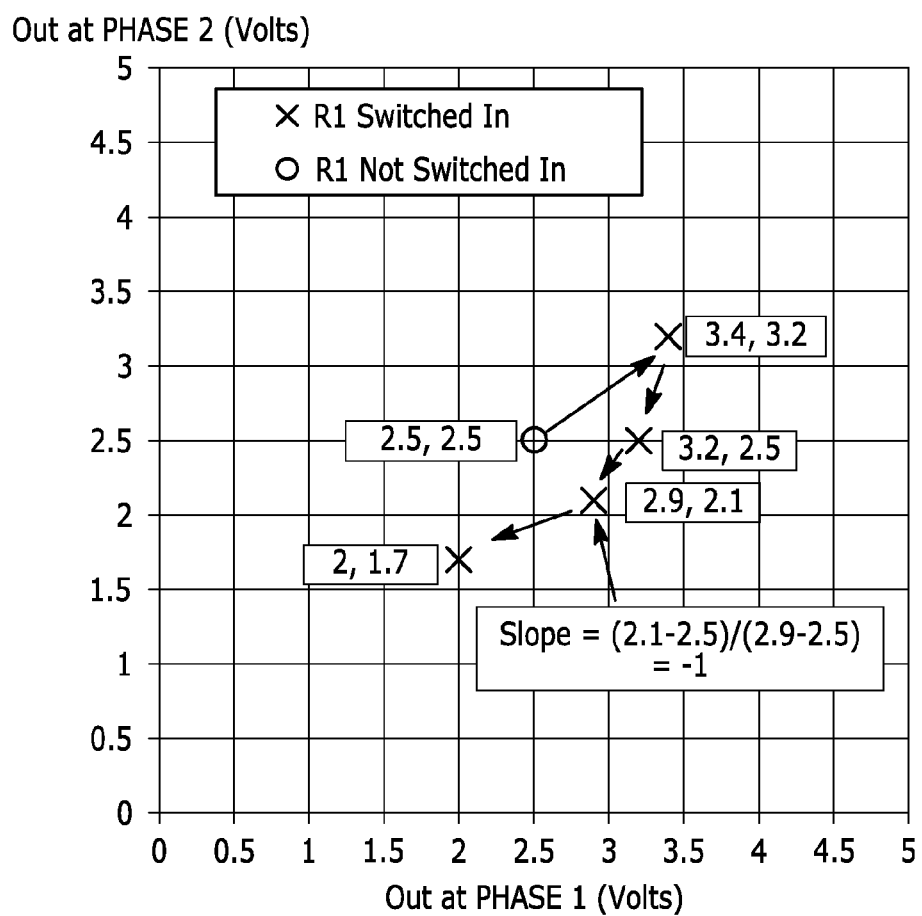
FIG. 8 is a graph illustrating changes in output voltages when a resistor is connected to the sensing node of the measurement circuit of FIG. 1 as measurement phases are incremented.

FIG. 8 is a graph illustrating example adjustments on the Phase1 and Phase2 signals with the switch for R1 closed and a blank switch (e.g., BL1) open. The arrows represent changes in the output for changes in the Phase1 and Phase2 signals between successive measurements (step 550 or 560). The coordinate pair (2.9, 2.1) depicts the target area where the slope is approximately equal to −1 from the coordinate pair without the resistor (R1) to the coordinate pair with the resistor (R1). Finding the phases where the slope is approximately −1 means that the average of Phase1 and Phase2 (i.e., (Phase1+Phase2)/2) is approximately the phase angle 90° from the angle of the change of the total current due to the current added when R1 is switched in. The negative slope is an indication that the two phases, Phase1 and Phase2, are on opposite sides of the phase angle 90° from the actual current change phase caused by switching in R1. Functionally, the two phases are chosen such that the output of the signal conditioning module 360 at one phase increases by approximately the same amplitude that the output at the other phase decreases when there is a parallel resistance switched in (e.g., R1). It should be noted that finding the phases where the slope is exactly −1 may not be necessary. Measurements may also be performed even when the calculated slope is significantly different than −1. As an example, a calculated slope anywhere in the range between −0.5 and −2 may give satisfactory results.

Figure 9:
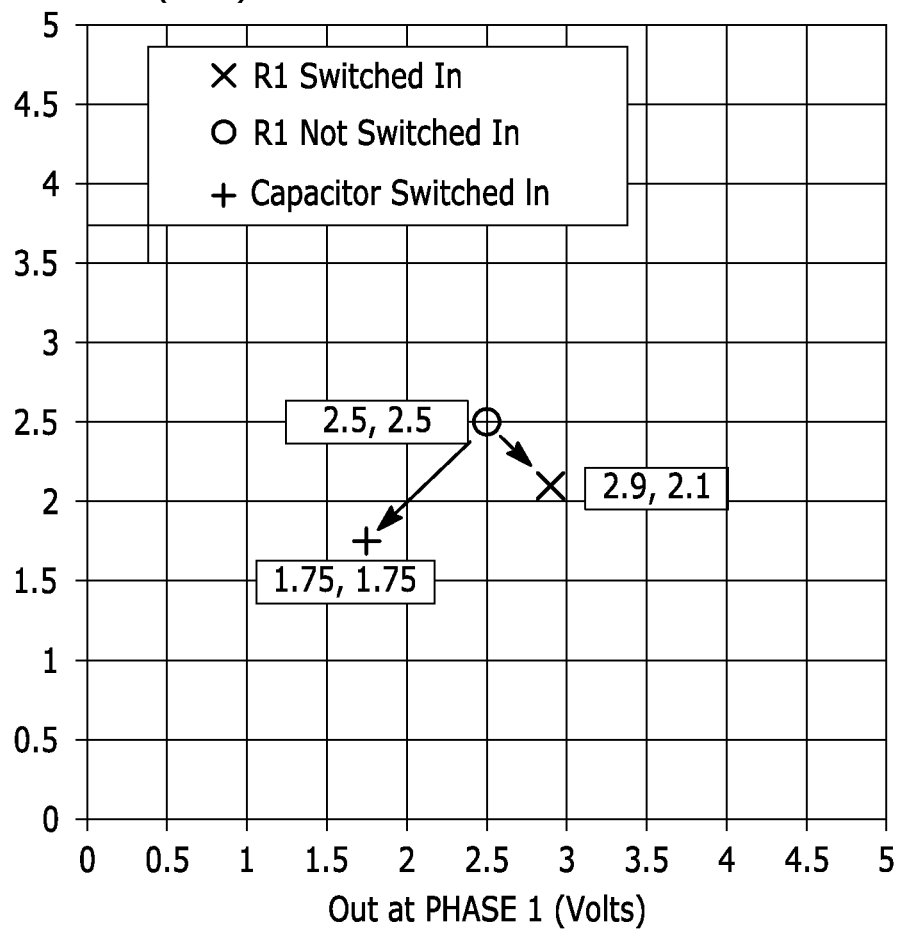
FIG. 9 is a graph illustrating changes in output voltages when a resistor and a capacitor are connected to the sensing node of the measurement circuit of FIG. 1.

FIG. 9 is a graph illustrating an example of the change in the output voltage of the signal conditioning module 360 that occurs as a parallel capacitor (C1) of the array of components 120 is switched in. In this case, an increase in current to the array of components 120 due to switching in a small parallel capacitance will decrease the current to and the voltage across the sensing component 130. For example, the coordinate pair (1.75, 1.75) of outputs of the signal conditioning module 360 for Phase1 and Phase2 has a lower voltage than the coordinate pair (2.5, 2.5) which does not have C1 switched in. The coordinate pair (1.75, 1.75) rests on a line with a slope of +1 to the coordinate pair (2.5, 2.5). FIG. 9 demonstrates that once the measuring circuit 100 is calibrated, switching the array of components 120 to add or remove purely capacitive components results in a change of the coordinates of the output of the signal conditioning module 360 such that the new coordinates will rest on a line with a slope of +1 from the previous coordinates. In other words, the measurement change due to an additional small parallel capacitance will lie on a line with a slope of +1, and the measurement change due to an additional parallel resistance will lie on a line with a slope of −1.

Figure 10:
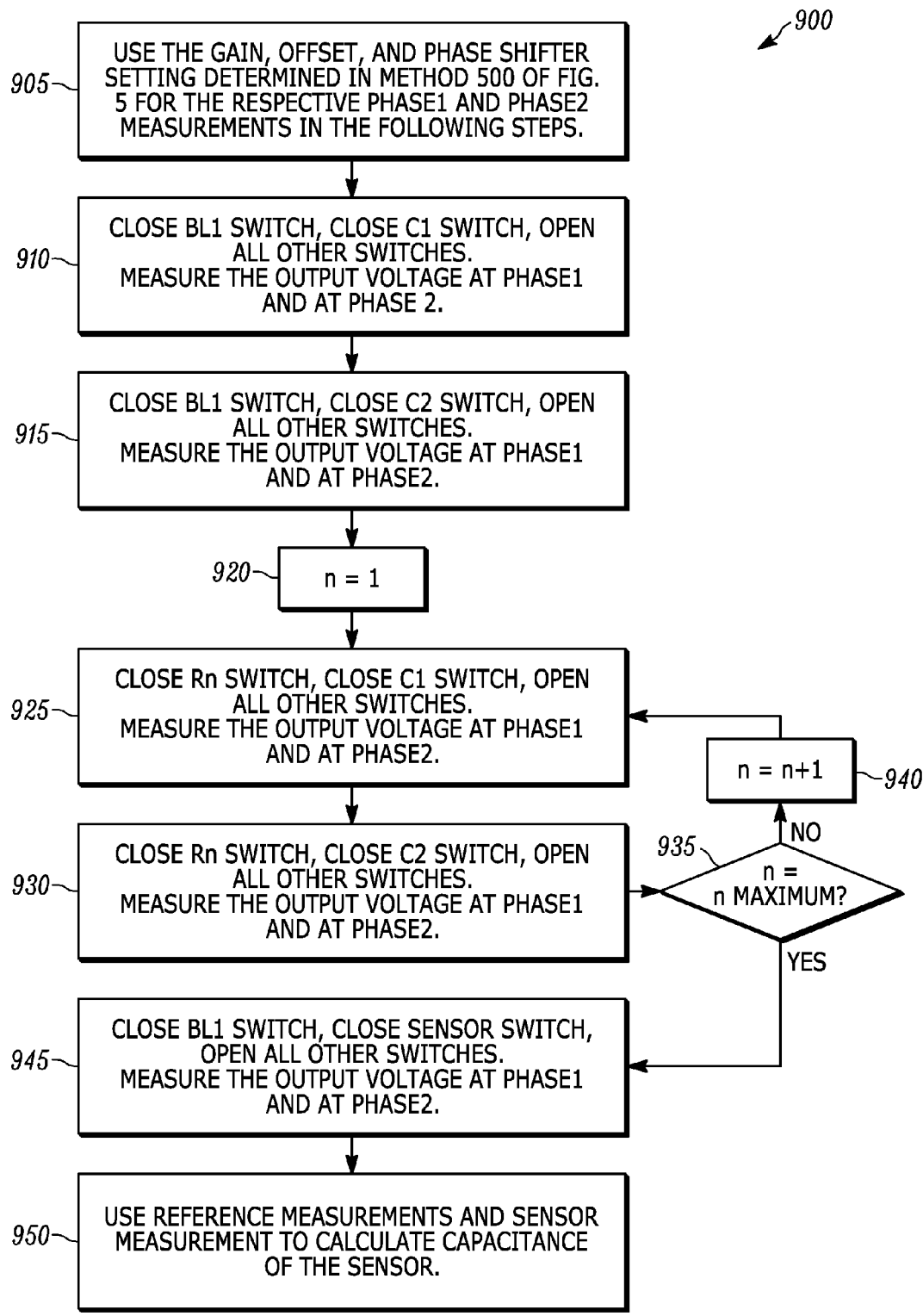
FIG. 10 is a flowchart of a method of measuring a capacitance of a sensor of the measuring circuit of FIG. 1.

FIG. 10 is a flowchart illustrating an exemplary measurement method 900 for the capacitance 220 of the sensor 125. Although illustrated in sequential order, steps of the measurement method 900 may be performed sequentially, simultaneously, or in a different order. In one example, measurement method 900 is performed at least in part by the controller 300. It is possible to perform parts of the measurement method 900 manually. Throughout the method 900, the gain and offset settings of the gain and offset adjustment module 160 are adjusted and the settings of the phase shifter 150 are adjusted to the settings determined in method 500 for each measurement (step 905). A blank switch (e.g., BL1) is closed, the switch for C1 is closed, all other switches of the switching array 115 are opened, and the output voltage of the analog-to-digital converter 165 at Phase1 and at Phase2 is measured (step 910). A blank switch (e.g., BL1) is closed, the switch for C2 is closed, all other switches of the switching array 115 are opened, and the output voltage of the analog-to-digital converter 165 at Phase1 and at Phase2 is measured (step 915). In the next step, n is set equal to 1, where n corresponds to a particular one of the resistors (R1, R2, . . . Rn) in the array of components 120 (step 920). The switch for Rn is closed, the switch for C1 is closed, all the other switches of the switching array 115 are opened, and the output voltage of the analog-to-digital converter 165 at Phase1 and at Phase2 is measured (step 925). The switch for Rn is closed, the switch for C2 is closed, all other switches of the switching array 115 are opened, and the output voltage of the analog-to-digital converter 165 at Phase1 and Phase2 is measured (step 930). In the next step, a determination of whether n equals n maximum (i.e., a highest numbered resistor) is made (step 935). This determination provides an indication of whether all the resistors in the array of components 120 have been used. If n does not equal n maximum, n is incremented by one (step 940). The method then proceeds to step 925. If n does equal n maximum, a blank switch (e.g., BL1) is closed, the switch for the sensor 125 is closed, all other switches of the switching array 115 are opened, and the output voltage of the analog-to-digital converter 165 at Phase1 and at Phase2 is measured (step 945). As will be described in greater detail, the reference measurements and the measurement of the sensor 125 (i.e., the measurements of the output voltages) are used to calculate the capacitance of the sensor 125 (FIG. 13).

Figure 11:
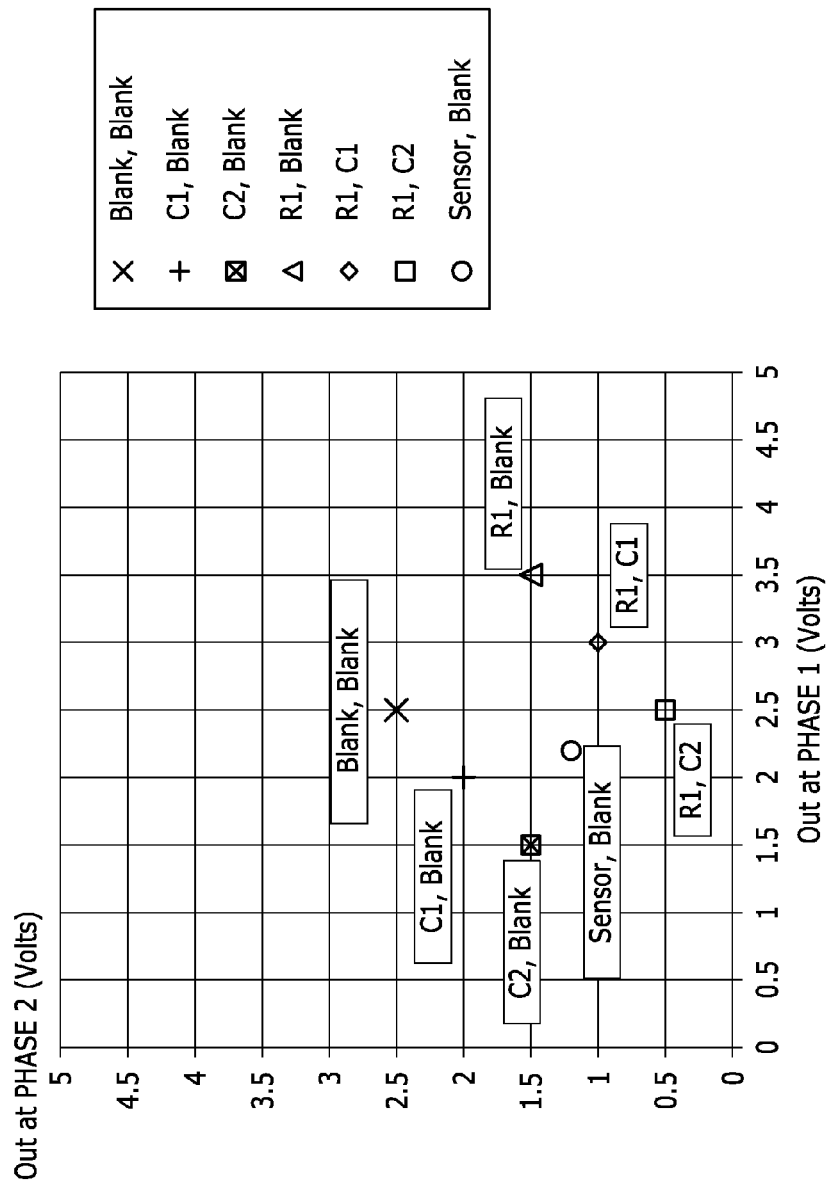
FIG. 11 is an exemplary graph of output voltages at multiple measurement phases with various components in connected to the sensing node.

FIG. 11 is a graph of an example of outputs of the measurement method 900 with only the output values generated with one resistor (R1) shown. Each graph will have different measured points depending on the reference values, the phase angles, the offset, and the gain of the system. The graph shown illustrates the measured outputs for the Phase1 and Phase2 signals (i.e., reference signals). Typically, the outputs are plotted for the coordinate pairs associated with each pairing of components from the array of components 120. Each of these outputs provides a set of reference signals corresponding to a different configuration of the array of components. An electrical characteristic of the fluid may be determined by comparing differences in values between the reference signals and the sensor signals. This includes plotting C1 and C2 with every resistor (R1, R2, . . . Rn) and plotting C1 and C2 with a blank switch (i.e., BL1 or BL2). Additionally, the resistors (R1, R2, . . . Rn) are plotted with a blank switch (i.e., BL1 or BL2). FIG. 11 illustrates that the capacitance changes are plotted on a line along a +1 slope from the coordinate pair (Blank, Blank), and the resistance changes are plotted on a line along a −1 slope from the coordinate pair (Blank, Blank). For example, the output change between the (C1, Blank) measurement and the (R1, C1) measurement is due to a change in parallel resistance, while the output change between the (C1, Blank) measurement and the (C2, Blank) measurement is due to a change in parallel capacitance. This behavior allows the resistance and the capacitance components of the sensor 125 to be separated and individually calculated as shown in FIG. 13.

Figure 12:
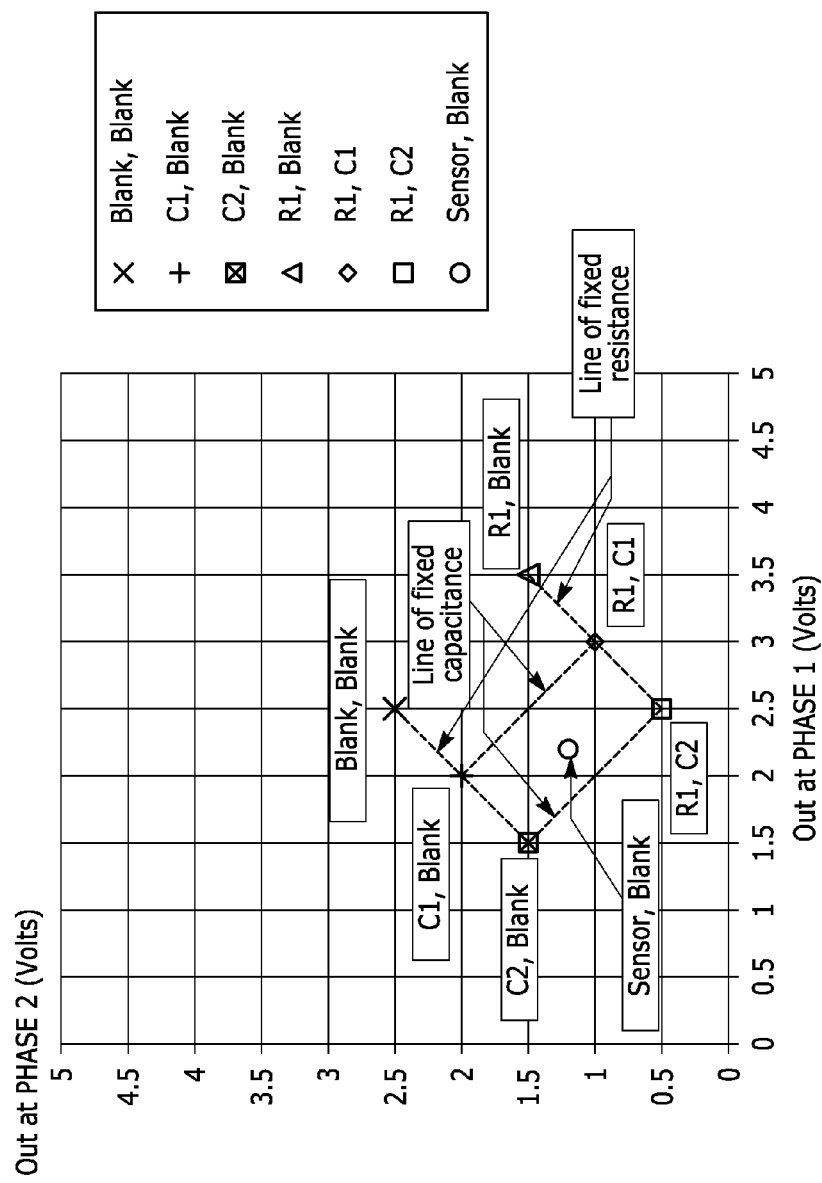
FIG. 12 is a graph illustrating parallel fixed lines of capacitance based on the output voltages of FIG. 11.

FIG. 12 is a graph illustrating parallel lines of fixed capacitance. As in FIG. 11, the graph illustrates the coordinate pairs of the outputs for the Phase1 and Phase2 signals for a plurality of components in parallel. The coordinate pairs create reference points to determine lines of fixed capacitance. For example, the coordinate pairs (C1, Blank) and (R1, C1) have the same capacitor, but the coordinate pair (R1, C1) adds a resistor (R1). A line that connects (C1, Blank) and (R1, C1) demonstrates a change in the components purely due to resistance, and therefore, represents a line of fixed capacitance. Similarly, a line that connects (C2, Blank) and (R1, C2) is a line of fixed capacitance. Lines of fixed resistance can also be determined. For example, a line of fixed resistance lies between the points (R1, C1) and (R1, C2).

Figure 13:
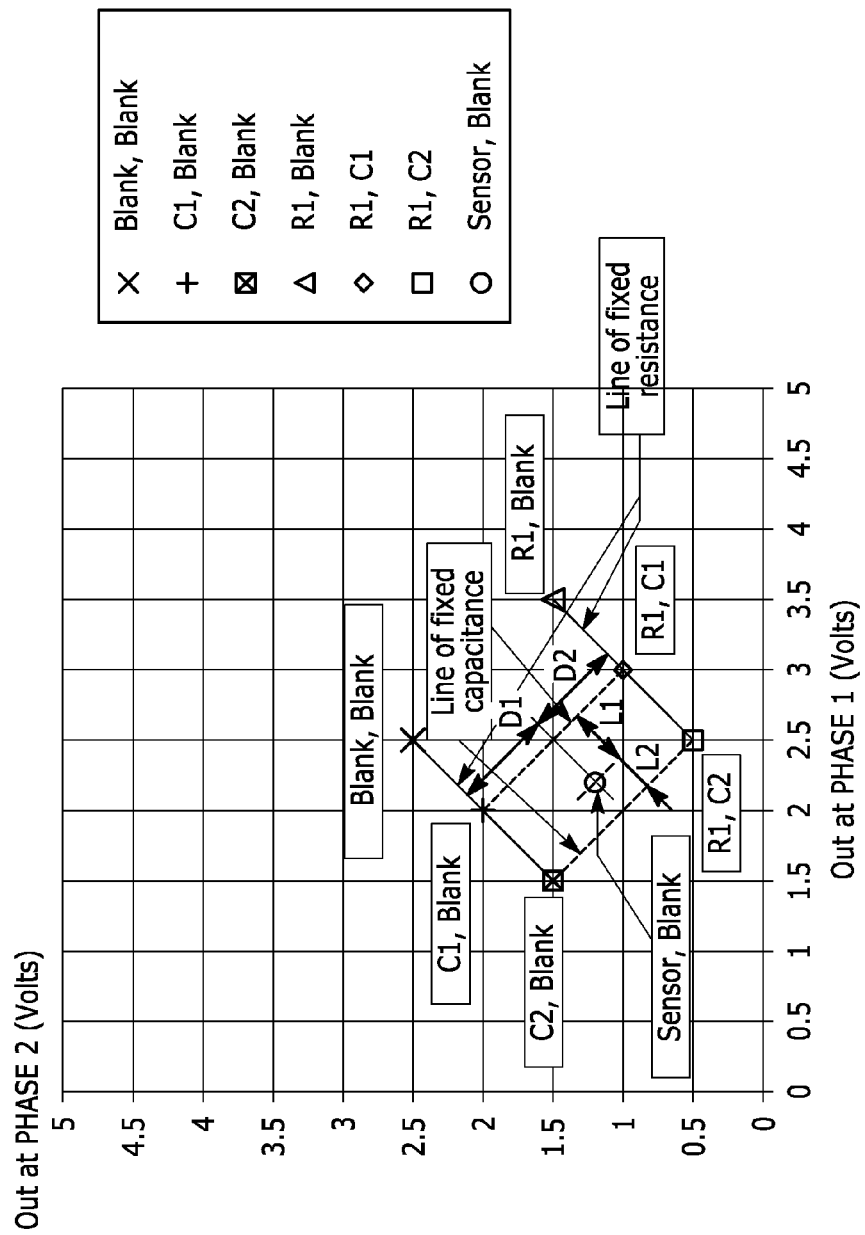
FIG. 13 is a graph illustrating interpolation between lines of fixed capacitance and lines of fixed resistance for determining the capacitance and the resistance of the fluid sensor with the measuring circuit of FIG. 1 according to one embodiment.

FIG. 13 is a graph illustrating interpolation between the lines of fixed capacitance for determining the capacitance of the sensor 125 according to one embodiment. Since the capacitance values for C1 and C2 are known, the capacitance values represented by the lines of fixed capacitance are also known. The capacitance of the sensor 125 is calculated by interpolating between the lines of fixed capacitance. This calculation can performed using Equation 6.

$$Csensor = L1 * \frac{C2 - C1}{L1 + L2} + C1 \qquad (6)$$

Where L1 and L2 are the distances from the lines of fixed capacitance to the measurement point of the sensor 125 and C1 and C2 are the capacitances in Farads of the reference capacitors. The calculation of the capacitance of the sensor 125 can be performed in a variety of ways once the measurements are performed. This equation is an example of one of the equations that can perform the interpolation, but the invention is not limited to this equation. It is also possible to use a single reference capacitor to make a measurement. In that case, a line of fixed capacitance extends between the points (Blank, Blank) and (R1, Blank). This line is a line of fixed capacitance of roughly zero. As noted above, a line of fixed capacitance extends between (C1, Blank) and (C1, R1). In this case, L1 is the distance between the line of roughly zero capacitance and the coordinate pair (Sensor, Blank), and L2 is the distance between the other line of fixed capacitance (for C1) and the coordinate pair (Sensor, Blank). In this case, the equation to calculate the capacitance of the sensor 125 simplifies to Equation 7.

$$Csensor = \frac{L1 * C1}{L1 + L2} \qquad (7)$$

The conductivity of the sensor 125 can also be measured with similar algorithms that use interpolation between lines of fixed resistance. For example, when each of the multiple resistors (R1, R2, . . . Rn) of the array of components 120 is switched in, a total resistance seen by the current source 105 may be calculated as shown in Equations 8 and 9.

$$Rtotalhigh = \frac{R * Rhigh}{R + Rhigh} \qquad (8)$$

$$Rtotallow = \frac{R * Rlow}{R + Rlow} \qquad (9)$$

Where R is a value of the resistance of the sensing component 130, Rhigh is the value of a resistor of the array of components 120 that corresponds to a line of fixed resistance with a higher value of resistance than the value of a resistance of the sensor 125, and Rlow is the value of a resistor of the array of components 120 that corresponds to a line of fixed resistance with a lower resistance than the sensor 125.

After the phases, offsets, and gain are determined, the distance is determined, in measurement units, between the line of fixed resistance that corresponds to the higher value of resistance and the measurement of the sensor 125 to find D1. Similarly, the distance is determined, in measurement units, between the line of fixed resistance that corresponds to the lower value of resistance and the measurement of the sensor 125 to find D2. The resistance of the sensor 125 in combination with the resistance of the sensing component 120 may then be determined by interpolation between the lines of fixed resistance as shown in Equation 10.

$$Rcombined = Rtotalhigh - \frac{D2 * (Rtotalhigh - Rtotallow)}{D1 + D2} \qquad (10)$$

The resistance of the sensor 125 may then be determined as shown in Equation 11.

$$Rsensor = \frac{R * Rcombined}{R - Rcombined} \quad (11)$$

Since the conductivity of the sensor 125 is not known prior to measurement, the plurality of resistors of the array of components 120 enables the measuring circuit 100 to measure capacitance of the sensor 125 over a large range of conductivities. This allows the system to focus the measurement space on values close to the actual values of the resistance and capacitance of the sensor 125. With a small enough resistor value, the measuring circuit 100 can achieve measurements when conductivities are well over 1000 µS/cm. A full measurement map characterizes the measurement system around, and near to, any values of the sensor 125. This results in an accurate capacitance measurement for various liquids even if their conductivities differ by more than a factor of one hundred.

Figure 14:
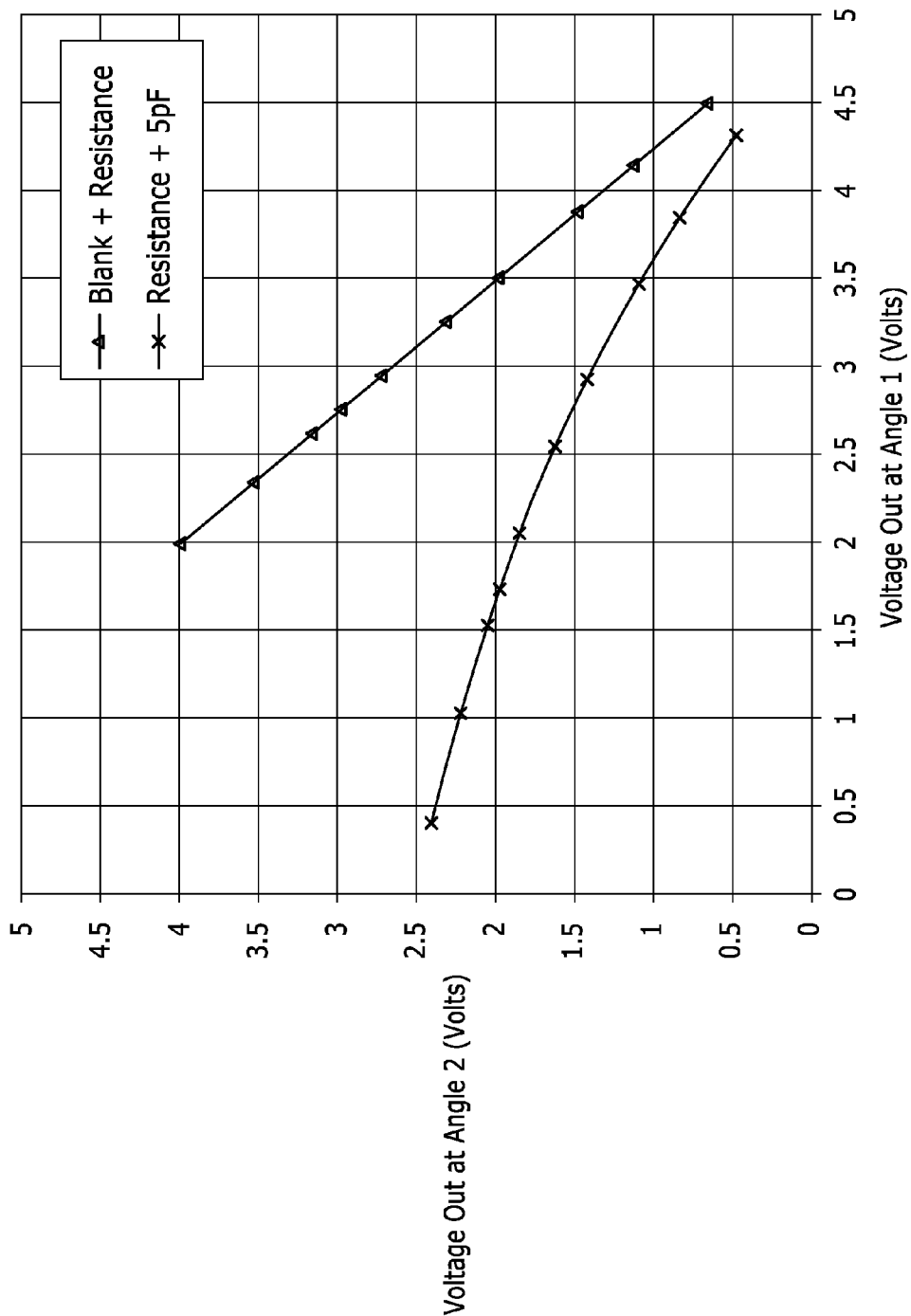
FIG. 14 is a graph illustrating non-linear effects of large changes in parallel resistance for the measuring circuit of FIG. 1.

FIG. 14 illustrates a change in output voltage over a wide range of parallel resistances according to one embodiment. Two lines of fixed capacitance are represented by two lines in the graph. The resistances range from 50Ω on the right side of the graph to $10^9 \Omega$ on the left side of the graph. As illustrated by approaching lines of fixed capacitance, the measurement space narrows as the parallel resistances get smaller. This causes a reduction in resolution at low parallel resistances. However, the gain and offset adjustment module 160 increases resolution and thus compensates for the loss of resolution. As shown in the graph, the lines of fixed capacitance can be straight or curved over a wide range of resistances. Using a plurality of reference resistors (e.g., R1, R2, etc.) in the array of components 120 that are in the range of resistances of the measurements reduces the effect of curvature of the lines of fixed capacitance. The lower the distance between lines of fixed resistance, the less error will be caused by a calculation based on the line segments of the lines of fixed capacitance. In this way, the curvature of the fixed lines of capacitance depend on the available levels of impedance of the array of components 120.

Figure 15:
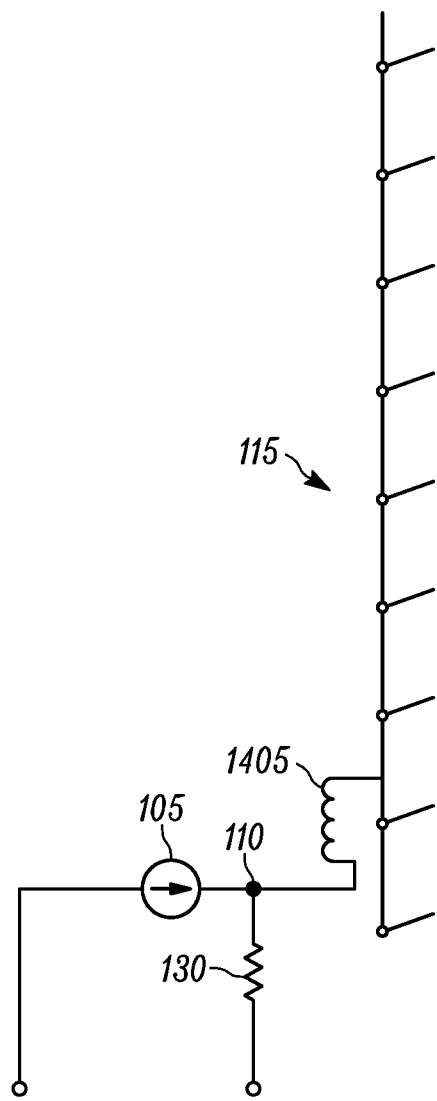
FIG. 15 is a schematic diagram of the measuring circuit of FIG. 1 including an inductor to balance parallel inductance in the circuit path of the sensor.

FIG. 15 illustrates an embodiment that compensates for the curvature of the lines of fixed capacitance. An inductor 1405 (e.g., 100 nH to 10,000 nH) is added between the sensing node 110 and the switching array 115. The inductor 1405 straightens out the curvature of the lines of fixed capacitance over a wide range of resistances, thereby improving straight-line approximation. Other embodiments have different additional components that are used to modify the response of the system. For example, an inductor 1405 may be added in series with the array of components 120 to adjust for inductance created by long leads to the sensor 125. In some embodiments, the algorithm to calculate capacitance using interpolation takes the curvature of the lines of fixed capacitance into account. For example, the curvature between the reference point measurements can be approximated by using measured values of three successive points at each line of fixed capacitance and deriving an appropriate curve for each line that passes through the measured points and that has a constant slope on either side of the center measurement point. If should be noted that multiple algorithms may be used to obtain a straight-line approximation of the lines of fixed capacitance.

Figure 16:
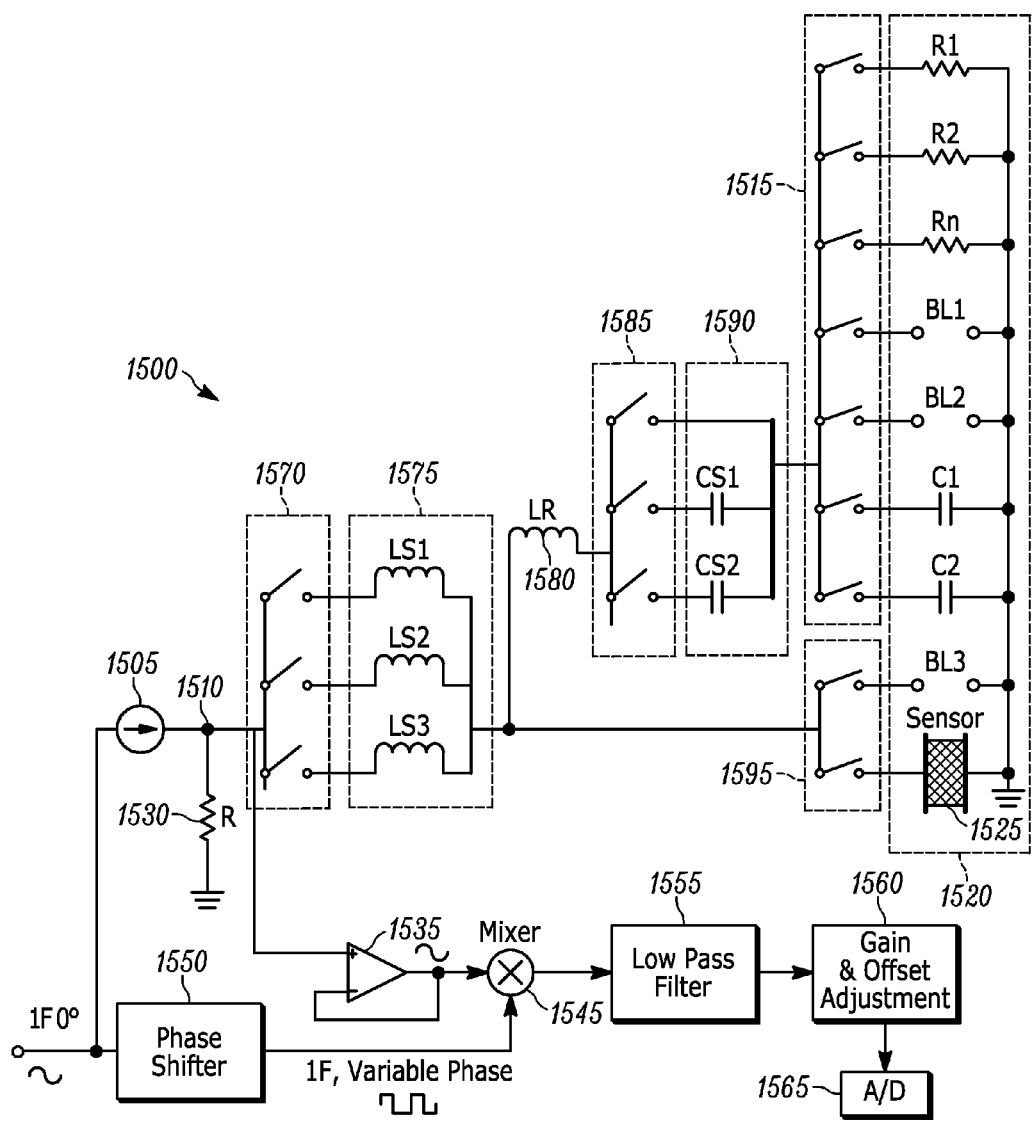
FIG. 16 is a block diagram of a measuring circuit for measuring capacitance and resistance of a fluid sensor in accordance with another embodiment.

FIG. 16 is a block diagram of another embodiment of a measuring circuit 1500. The measuring circuit 1500 includes a current supply 1505 connected to a sensing node 1510, a switching array 1515, an array of components 1520, and a sensing component 1530 (e.g., a resistor). The measuring circuit 1500 also includes a buffer amplifier 1535, a mixer 1545, a low-pass filter 1555, a gain and offset module 1560, and an analog-to-digital converter 1565. In these respects, the measuring circuit 1500 is similar to the measuring circuit 100. However, the measuring circuit 1500 includes multiple switchable impedances in a series-type connection with the array of components 1520. In particular, the measuring circuit 1500 includes an inductance switching array 1570, an array of inductors 1575, a series inductor 1580, a capacitance switching array 1585, an array of capacitors 1590, and a sensor switching array 1595.

The inductance switching array 1570 is controllable by the controller 300 to select various inductance values from the array of inductors 1575 to place in a series-type connection with the array of components 1520 and the sensor switching array 1595. Similarly, the capacitance switching array 1585 is controllable by the controller 300 to select various capacitance values from the array of capacitors 1590 to place in a series-type connection with the array of components 1520. The sensor switching array 1595 is controllable by the controller 300 to select either a sensor 1525 or a blank switch (e.g., BL3). In addition, the series inductor 1580 is connected between the array of inductors 1575 and the capacitance switching array 1585.

The measuring circuit 1500 is able to compensate for low levels of total capacitance across the sensor 125 caused by low values of induced capacitance 240 on the sensor 125 (see FIG. 3C). When the induced capacitance 240 becomes so low such that the reference impedances of the array of components 1520 no longer have absolute values similar to the total capacitance of the sensor 125, the controller 300 switches in series capacitance using the capacitance switching array 1585. The addition of capacitor CS1 and capacitor CS2 of the array of capacitors 1590 allow a capacitance to be inserted in series with the reference impedance from the array of components 1520. In this way, the total impedance measured during the reference measurements is in a similar range as the total capacitance of the sensor 125. The controller 300 is configured to determine which value of capacitance should be inserted in series with the array of components 1520 by making measurements and calculating the difference between the calculated capacitance at a first frequency and the calculated capacitance at a second frequency. For example, if the difference is above a threshold then the controller 300 switches in a smaller valued capacitor from the array of capacitors 1590. Other algorithms may also be used to decide which capacitor should be inserted in series. In addition, the controller 300 switches the inductance switching array 1570 to place an inductor LS1, an inductor LS2, and an inductor LS3 from the array of inductors 1575 in various combinations into a series-type connection with the array of components 1520 and the sensor switching array 1595. The inductance switching array 1570 enables the controller 300 to match the appropriate series inductance with the selected series capacitance to straighten the response curves as discussed above.

It should be noted that the sensor switching array 1595 may be separate from the switching array 1515 and that the sensor switching array 1595 is switchable with its own blank switch BL3, as illustrated in FIG. 16. When the reference impedances of the array of components 1520 are being measured, the blank switch BL3 is closed and a sensor switch of the sensor switching array 1595 for switching in the sensor 1525 is open. When the sensor 1525 is being measured, the blank switch BL3 is open, the reference blank switches, BL1 and BL2, are closed, and the sensor switch is closed. In this way, the measuring circuit 1500 controls the sensor switching array 1595 and the switching array 1515 such that the parasitic capacitance is held constant throughout the measurement method 900.

It should be noted that although the circuit described here uses a current source 105, a sensing component 130, and a buffer amplifier 135 as the electronics used to create the measurement signal, other variations of measuring circuits may be used to create the measurement signal. For example, in some embodiments, an oscillating voltage source and an alternative method of measuring the sensing current may be used. The variable phase signal may then be mixed with the measurement signal as described by the methods disclosed herein.

It should also be noted that embodiments may also be used to measure the resistive and reactive components of impedances not associated with a fluid sensor. For example, embodiments may be used to measure the impedance of biological tissue or other industrial applications where a high frequency measurement is desired.

Once the capacitance of the sensor 125 is determined by using the above-described methods and circuits, the dielectric constant of the fluid can be calculated using Equation 12.

$$k = \frac{C_{sensor} - C_{offset}}{X} \quad (12)$$

The $C_{offset}$ is the portion of the measured capacitance that does not change with the dielectric constant. X is determined by measuring a capacitance of the sensor 125 with each of two fluids of known dielectric constant (k1 and k2). $C_{sensor1}$ is a capacitance of the sensor 125 when the first fluid is measured and $C_{sensor2}$ is the capacitance of the sensor 125 when the second fluid is measured. X may be determined using Equation 13.

$$X = \frac{C_{sensor1} - C_{sensor2}}{k1 - k2} \quad (13)$$

The dielectric constant of the fluid may then be used to determine other characteristics of the fluid. For example, the concentration or quality levels of the fluid.

Thus, the invention provides, among other things, a system and a method for determining capacitance and resistance of a fluid sensor, especially when a low-resistance path lies in parallel to the capacitance. Various features and advantages of the invention are set forth in the following claims.

What is claimed is:

1. A system for measuring an electrical characteristic of a fluid by separating a first orthogonal component of a signal change of a measurement signal and a second orthogonal component of the signal change of the measurement signal, where the first orthogonal component is due to a change in resistance across a sensor and the second orthogonal component is due to a change in capacitance across the sensor, the system comprising:
   an array of components including the sensor;
   a mixer that mixes the measurement signal with a first phase signal and a second phase signal, the mixer outputting a first mixed signal related to the first phase signal and a second mixed signal related to the second phase signal; and
   a controller that is configured to
      receive a signal indicative of the first mixed signal and the second mixed signal;
      control the array of components to cause the signal change;
      adjust the first phase signal and the second phase signal such that when there is a change in the first orthogonal component, the first mixed signal is increased and the second mixed signal is reduced;
      control the array of components to cause additional signal changes;
      receive a plurality of mixed signals indicative of the additional signal changes at the first phase and the second phase;
      determine the electrical characteristic of the fluid based on the plurality of mixed signals.

2. The system of claim 1, wherein the electrical characteristic of the fluid is a dielectric constant and a conductivity of the fluid.

3. The system of claim 1, wherein the controller is further configured to identify measures that are related to a dielectric constant and a conductivity of the fluid based on the plurality of mixed signals.

4. The system of claim 1, wherein the controller is further configured to measure a resistance and reactance of the sensor based on the plurality of mixed signals.

5. The system of claim 1, further comprising a phase shifter connected to the mixer, the phase shifter configured to output and adjust the first phase signal and the second phase signal based on an adjustment signal from the controller.

6. The system of claim 5, wherein the controller is further configured to:
   perform a calibration of the first phase signal and the second phase signal before determining the electrical characteristic of the sensor, wherein, during calibration, the controller is configured to
      measure, at a first calibration impedance, a first calibration signal when the first phase signal is input to the mixer and a second calibration signal when the second phase signal is input to the mixer;
      measure, at a second calibration impedance, a third calibration signal when the first phase signal is input to the mixer and a fourth calibration signal when the second phase signal is input to the mixer; and
      adjust the first phase signal and the second phase signal based on the first calibration signal, the second calibration signal, the third calibration signal, and the fourth calibration signal.

7. The system of claim 1, wherein the array of components includes a plurality of resistors.

8. The system of claim 1, wherein the array of components includes at least one capacitor, at least one resistor, and at least one blank switch.

9. The system of claim 1, further comprising a switchable array of capacitors in a series-type connection connected to the array of components.

10. The system of claim 9, further comprising a switchable array of inductors in a series-type connection connected to the array of components.

11. The system of claim 10, further comprising an offset inductor in a series-type connection connected between the array of inductors and the array of capacitors.

12. A method of measuring an electrical characteristic of a fluid with a measuring circuit that includes a sensing node, a sensor switchably connected to the sensing node, and an array of components switchably connected to the sensing node, and a controller, the method comprising:
   mixing a signal indicative of a voltage at the sensing node at a first configuration of the array of components with a first phase signal and a second phase signal to create a first set of reference signals;
   mixing the signal at a second configuration of the array of components with the first phase signal and the second phase signal to create a second set of reference signals;
   adjusting the first phase signal and the second phase signal until a relationship between the first set of reference signals and the second set of reference signals satisfies a condition;
   setting a plurality of configurations of the array of components;
   mixing the signal with the adjusted first phase signal and the adjusted second phase signal at each of the plurality of configurations of the array of components to create a plurality of sets of reference signals;
   mixing the signal with the adjusted first phase signal and the adjusted second phase signal with the sensor connected to the sensing node to create a set of measurement voltages;
   determining the electrical characteristic of the fluid based on a relationship between the plurality of sets of reference signals and the set of measurement voltages.

13. The method of claim 12, wherein determining the electrical characteristic of the fluid includes identifying measures that are related to the dielectric constant and the conductivity of the fluid based on the relationship between the plurality of sets of reference signals and the set of measurement voltages.

14. The method of claim 12, wherein determining the electrical characteristic of the fluid includes determining a resistance and a reactive impedance of the sensor based on the plurality of sets of reference signals and the set of measurement voltages.

15. The method of claim 12, wherein adjusting the first phase and the second phase until a relationship between the first set of reference signals and the second set of reference signals satisfies a condition includes determining when a voltage change between the first set of reference signals and the second set of reference signals indicates a resistance change orthogonal to a capacitance change.

16. The method of claim 12, wherein adjusting the first phase and the second phase until a relationship between the first set of reference signals and the second set of reference signals satisfies a condition includes determining a slope of a line extending between the first set of calibration voltages and the second set of calibration voltages.

17. The method of claim 16, wherein the relationship is having a line between the first set of calibration voltages and the second set of calibration voltages with a slope approximately equal to −1.

18. The method of claim 12, further comprising:
   mixing the signal at a third configuration of the array of components with the first phase signal and the second phase signal to create a third set of reference signals;
   mixing the signal at a fourth configuration of the array of components with the first phase signal and the second phase signal to create a fourth set of reference signals;
   mixing the signal at a fifth configuration of the array of components with the first phase signal and the second phase signal to create a fifth set of reference signals;
   mixing the signal at a sixth configuration of the array of components with the first phase signal and the second phase signal to create a sixth set of reference signals; and
   determining the electrical characteristic of the fluid by comparing a difference in value of the set of sensor voltages with the third set of reference signals, the fourth set of reference signals, the fifth set of reference signals, and the sixth set of reference signals.

19. The system of claim 18, wherein determining the electrical characteristic of the fluid by comparing a difference in value of the set of sensor voltages with the third set of reference signals, the fourth set of reference signals, the fifth set of reference signals, and the sixth set of reference signals includes
   determining a first line of fixed capacitance between the third set of reference signals and the fourth set of reference signals;
   determining a second line of fixed capacitance between the fifth set of reference signals and the sixth set of reference signals; and
   determining a capacitance of the sensor by interpolating between the first line of fixed capacitance and the second line of fixed capacitance.

20. A system for measuring an electrical characteristic of a fluid, the system comprising:
   a sensing node;
   a sensor connected, via a switching array, to the sensing node;
   an array of components connected, via the switching array, to the sensing node, the array of components including a plurality of impedances;
   a monitoring circuit connected to the sensing node, the monitoring circuit configured to input a plurality of signals at a plurality of phases and output a signal related to a measurement signal at the sensing node; and
   a controller connected to the switching array and the monitoring circuit, the controller configured to
   receive the plurality of signals,
   set a first phase and a second phase of an input signal to the monitoring circuit;
   measure, at a first calibration impedance of the plurality of impedances, a first calibration voltage at the first phase and a second calibration voltage at the second phase;
   measure, at a second calibration impedance of the plurality of impedances, a third calibration voltage at the first phase and a fourth calibration voltage at the second phase;
   adjust the first phase and the second phase until a relationship between the first calibration voltage, the second calibration voltage, the third calibration voltage, and the fourth calibration voltage satisfies a condition;
   adjust the plurality of impedances by controlling the switching array to connect at least one component of the array of components to the sensing node in a parallel-type connection,
   determine a first set of reference signals based on the signal when the switching array is configured to couple a first measuring impedance of the plurality of impedances to the sensing node;
   determine a second set of reference signals based on the signal when the switching array is configured to couple a second measuring impedance of the plurality of impedances to the sensing node;

determine a set of sensor voltages based on the signal when the switching array is configured to couple the sensor to the sensing node, and determine an electrical characteristic of the sensor based on the first set of reference signals, the second set of reference signals, and the set of sensor voltages.

* * * * *